(12) United States Patent
Cardarelli et al.

(10) Patent No.: US 7,662,381 B2
(45) Date of Patent: Feb. 16, 2010

(54) INTERFERON ALPHA RECEPTOR 1 ANTIBODIES AND THEIR USES

(75) Inventors: Josephine M. Cardarelli, San Carlos, CA (US); Alison Witte, Scotts Valley, CA (US); Mohan Srinivasan, San Jose, CA (US)

(73) Assignee: Medarex, Inc., Princeton, NJ (US)

( * ) Notice: Subject to any disclaimer, the term of this patent is extended or adjusted under 35 U.S.C. 154(b) by 0 days.

(21) Appl. No.: 11/157,494

(22) Filed: Jun. 20, 2005

(65) Prior Publication Data

US 2006/0029601 A1    Feb. 9, 2006

Related U.S. Application Data

(60) Provisional application No. 60/581,747, filed on Jun. 21, 2004.

(51) Int. Cl.
*A61K 39/395* (2006.01)
*C12P 21/08* (2006.01)

(52) U.S. Cl. .................. 424/143.1; 530/388.22

(58) Field of Classification Search ........................ None
See application file for complete search history.

(56) References Cited

U.S. PATENT DOCUMENTS

| | | | |
|---|---|---|---|
| 5,516,515 A | 5/1996 | Vellucci et al. | |
| 5,731,169 A | 3/1998 | Mogensen et al. | |
| 5,861,258 A | 1/1999 | Mogensen et al. | |
| 5,886,153 A | 3/1999 | Mogensen et al. | |
| 5,889,151 A | 3/1999 | Mogensen et al. | |
| 5,919,453 A * | 7/1999 | Benoit et al. | 424/143.1 |
| 6,458,932 B1 | 10/2002 | Novick et al. | |
| 6,713,609 B1 * | 3/2004 | Chuntharapai et al. | 530/388.22 |
| 6,787,634 B2 | 9/2004 | Benoit et al. | |
| 7,179,465 B2 | 2/2007 | Benoit et al. | |
| 7,465,451 B2 | 12/2008 | Benoit et al. | |
| 2003/0044410 A1 | 3/2003 | Skurkovich et al. | |
| 2003/0166228 A1 | 9/2003 | Chuntharapai et al. | |
| 2004/0067888 A1 | 4/2004 | Tovey et al. | |
| 2005/0152901 A1 | 7/2005 | Pickford et al. | |
| 2005/0208041 A1 | 9/2005 | Cardarelli et al. | |
| 2007/0014724 A1 | 1/2007 | Witte et al. | |

FOREIGN PATENT DOCUMENTS

| | | |
|---|---|---|
| EP | 0369877 | 5/1990 |
| EP | 0563487 A1 | 10/1993 |
| WO | WO 91/05862 | 5/1991 |
| WO | WO93/20187 | 10/1993 |
| WO | WO94/14467 | 7/1994 |
| WO | WO95/07716 | 3/1995 |
| WO | WO 97/41229 | 11/1997 |
| WO | WO 98/24884 | 6/1998 |
| WO | WO 98/52976 | 11/1998 |

(Continued)

OTHER PUBLICATIONS

Eid et al., European Cytokine Network. Dec. 2000; 11(4):560-73.*

(Continued)

*Primary Examiner*—Cherie M Woodward
(74) *Attorney, Agent, or Firm*—Baker Botts L.L.P.

(57) ABSTRACT

The present invention provides isolated human monoclonal antibodies that bind to IFNAR-1 and that are capable of inhibiting the biological activity of Type I interferons. Immunoconjugates, bispecific molecules and pharmaceutical compositions comprising the antibodies of the invention are also provided. The invention also provides methods for inhibiting Type I interferon-mediated disorders using the antibodies of the invention, including methods for treating autoimmune disorders, transplant rejection or Graft Versus Host Disease using the antibodies of the invention.

20 Claims, 15 Drawing Sheets

FOREIGN PATENT DOCUMENTS

| WO | WO 99/39211 | 8/1999 |
|----|----|----|
| WO | WO 00/53635 | 9/2000 |
| WO | WO 01/09187 | 2/2001 |
| WO | WO 01/14424 | 3/2001 |
| WO | WO 01/54721 | 8/2001 |
| WO | WO 01/55215 | 8/2001 |
| WO | WO 02/43428 A2 * | 6/2002 |
| WO | WO 02/43478 | 6/2002 |
| WO | WO 02/066649 | 8/2002 |
| WO | WO 2004/093908 | 11/2004 |

OTHER PUBLICATIONS

Goldman et al., J Interferon and Cytokine Research. 1999; 19:15-26.*
Lu et al., J lmmunol. Feb. 15, 1998;160(4):1782-8.*
Gahring et al., Autoimmunity. 1998; 28:243-248.*
Pritsch et al., British J Haematol. 1999; 107:616-624.*
Li et al., J Mol Biol. Mar 1, 1996;256(3):577-89.*
Miller et al., J Rheumatol. Dec. 1995;23(12)2132-9, Abstract Only.*
Martin et al., J lmmunol. Jun. 15, 1994; 152(12)5988-96, Abstract Only.*
Scott et al., J Immunol. Dec. 1991; 147(11):4007-4013.*
UniProt Accession No. P17181, INAR1__Human.*
Lederman et al. Mol Immunol. 1991;28:1171-1181.*
Li et al. PNAS USA. 1980; 77:3211-3214.*
Fishwild et al., Nature Biotechnology. 1996;14:845-851.*
Mayo et al., Stats Med. 1999;18:223-231.*
Ohlin et al., Mol Immunol. May-Jun. 1996;33(7-8):583-92, Abstract only.*
Lu et al., (J Immunol. 1998. 160:1782-1788).*
Geysen et al., (J Mol Recog. 1988;1(1):32-41).*
Short et al., (Protein Engineering. 2001;14(4):287-296).*
Chen et al., (J Exp Med. Sep. 1, 1992;176:885-866).*
Lewerenz et al., (J Mol Biol. Sep. 25, 1998;282(3):585-599).*
Chen, et al., EMBO J. 1993; 12:811-820.
Cook et at, J Biol Chem, 1996;271:13448.
Cutrone and Langer, J Biol Chem. 2001;276:17140.
Fishwild et al., Nature Biotechnology 1996;14:845-851.
Foulis et al., Lancet. 1987;2:1423.
Hardy et al., Blood. 2001;97:473.
Hooks et al., Arthritis Rheum. 1982;25:396.
Lewerenz et at, J Mol Biol. 1998;282:585.
Lonberg et al., Nature. 1994;368(6474):856-859.
Novick et al., Cell. 1994;77:391.
Santini et al., J Exp Med. 2000;191:1777.
Streuli et al., Proc Natl Acad Sci USA. 1981;78:2848.
Uze et al. Cell. 1990;225.
Goldman et al., "Characterization Of Antihuman IFNAR-1 Monclonal Antibodies: Epitope Localization and Functional Analysis," Journal of Interferon And Cytokine Research, 19:15-26 (1999).
Abramovich, et al., 1992, "Human IFN-ALPHA Receptor Detected by Two Monoclonal Antibodies," *Journal of Interferon Research*, vol. 12, No. Suppl 1.: p. S217.
Benizri, et al., 1998, "Prolonged Allograft Survival In Cynomolgus Monkeys Treated With A Monoclonal Antibody To The Human Type I Interferon Receptor And Lowdoses Of Cyclosporine," *Journal of Interferon and Cytokine Research*, vol. 18: p. 273-284.
Benoit, et al., 1993, "A Monoclonal Antibody To Recombinant Human IFN-ALPHA Receptor Inhibits Biologic Activity Of Several Species of Human IFN-ALPHA, IFN-BETA, and IFN-ONIEGA. Decection Of Heterogeneity Of The Cellular Type I IFN Receptor," *Journal of Immunology*, vol. 150, No. 3: p. 707-716.
Colamonici, et al., 1990, "Characterization Of Three Monoclonal Antibodies That Recognize The Interferon ALPHA2 Receptor," *Proceedings of the National Academy of Sciences of USA*, vol. 87, No. 18: p. 7230-7234.
Constantinescu, et al., 1994, "Role Of Interferon ALPHA/BETA Receptor Chain 1 In The Structure and Transmembrane Signaling Of The Interferon ALPHA/BETA Receptor Complex," *Proceedings of the National Academy of Sciences of USA*, vol. 91, No. 20: 9602- 606.

Novick, et al., 2000, "The Neutralization Of Type I IFN Biologic Actions By Anti-IFNAR-2 Monoclonal Antibodies Is Not Entirely Due To Inhibition Of Jak-Stat Tyrosine Phosphorylation," *Journal of Interferon and Cytokine Research*, vol. 20, No. 11: p. 971-982.
Aguet et al., "Interferon 5" Ed. I. Gresser p. 1-22, Academic Press, London (1983).
Amin et al., "Innovations in Pharmaceutical Technology," Samedan Ltd, publishers, Jun. 2002.
Arvin AM and Miller JJ 3rd, "Acid labile alpha-interferon in sera and synovial fluids from patients with juvenile arthritis," Arthritis Rheum. May 1984;27(5):582-5.
Blanco P, et al., "Induction of dendritic cell differentiation by IFN-alpha in systemic lupus erythematosus," Science. Nov. 16, 2001;294(5546):1540-3.
Branca AA "Bovine spleen, a convenient source for purifying a type I interferon receptor," J. Interferon Res. 7(1):77-85 (1987).
Brinkmann V, et al., "Interferon alpha increases the frequency of interferon gamma-producing human CD4+ T cells," J Exp Med. Nov. 1, 1993;178(5):1655-63.
Brown M, et al., "Tolerance of single, but not multiple, amino acid replacements in antibody VH CDR 2: a means of minimizing B cell wastage from somatic hypermutation?" J Immunol. May 1, 1996;156(9):3285-91.
Casset F, et al., "A peptide mimetic of an anti-CD4 monoclonal antibody by rational design," Biochem Biophys Res Commun. Jul. 18, 2003;307(1):198-205.
Chuntharapai A, et al., "Characterization and humanization of a monoclonal antibody that neutralizes human leukocyte interferon: a candidate therapeutic for IDDM and SLE," Cytokine. Sep. 7, 2001;15(5):250-60.
Cohen RD, "Evolving medical therapies for ulcerative colitis," Curr Gastroenterol Rep. Dec. 2002;4(6):497-505.
Colamonici et al, "Characterization of three monoclonal antibodies that recognize the interferon alpha 2 receptor," Proc. Natl. Acad. Sci USA 87(18):7230-34 (1990).
Colman PM, "Effects of amino acid sequence changes on antibody-antigen interactions," Res Immunol. Jan. 1994;145(1):33-6.
Corssmit EP, et al., "Effects of interferon-alpha (IFN-alpha) administration on leucocytes in healthy humans," Clin Exp Immunol. Feb. 1997;107(2):359-63.
Deavin AJ, et al., "Statistical comparison of established T-cell epitope predictors against a large database of human and murine antigens," Mol Immunol. Feb. 1996;33(2):145-55.
Dunbar BS and Schwoebel ED, "Preparation of polyclonal antibodies," Methods in Enzymology (1990);182:663-70.
Eid et al, J. Interferon Res. 7(6):762 (1987).
Eid et al, Biochem. Biophys. Acta 1034(1):114-117 (1990).
Eid et al., "Characterization of a Domain of Human Type I Interferon Receptor Protein Involved in Ligand Binding", J. Interferon Cytokine Research, 15:205-211 (1995).
Epstein et al, Biochemical and Biophysical Research Communications, 107(3):1060-1066 (Aug. 16, 1982), Academic Press, Inc., (New York, US) "Direct evidence that the gene product of the human chromosome 21 locus, IFRC, is the interferon-alpha receptor".
Fais et al., Interferon Res. Oct. 1994; 14(5):235-8.
Faltynek et al., Proc. Acad. Sci., 80, 3269, Jun. 1983.
Finkelman FD, et al., "Regulation by interferon alpha of immunoglobulin isotype selection and lymphokine production in mice," J Exp Med. Nov. 1, 1991;174(5):1179-88.
Gaboriaud et al, FEBS 269(1):1-3 (1990).
Haller O, et al., "Virus-specific interferon action. Protection of newborn Mx carriers against lethal infection with influenza virus," J Exp Med. Jul. 1, 1981;154(1):199-203.
Harris, W. J. et al, TIBTECH, 11:42-44, Feb. 1993.
Hertzog PJ, et al., "Interferons in rheumatoid arthritis: alterations in production and response related to disease activity," Clin Immunol Immunopathol. Aug. 1988;48(2):192-201.
Hopkins SJ and Meager a. "Cytokines in synovial fluid: II. The presence of tumour necrosis factor and interferon," Clin Exp Immunol. Jul. 1988;73(1):88-92.

Huang Z, "Structural chemistry and therapeutic intervention of protein-protein interactions in immune response, human immunodeficiency virus entry, and apoptosis," Pharmacol Ther. Jun. 2000;86(3):201-15.

Janeway et al., Immunobiology, p. 3.2. Garland Science, New York, 1997.

Janeway et al., Immunobiology, 5th Ed., Garland Science, pp. 116-117 (2001).

Langer et al., "Interferon Receptors", Immun. Today, vol. 9, No. 12, Dec. 1988, pp. 393-400.

Langer et al, Somatic Cell & Molecular Genetics 16(3):231-240 (1990).

Langer et al , BBRC 157(3):1264-1270 (1988).

Larrick et al, Biotechniques, pp. 6-14, Jan.-Feb. 1984.

Lindenmann J, "Induction of chick interferon: procedures of the original experiments," Methods Enzymol. 1981;78(Pt A):181-8.

Luft T, et al., "Type I IFNs enhance the terminal differentiation of dendritic cells," J Immunol. Aug. 15, 1998;161(4):1947-53.

Luft T, et al., "IFN-alpha enhances CD40 ligand-mediated activation of immature monocyte-derived dendritic cells," Int Immunol. Apr. 2002;14(4):367-80.

Lutfalla et al, J. Biol. Chem. 267(4):2802-09 (1992).

MacCallum RM, et al., "Antibody-antigen interactions: contact analysis and binding site topography," J Mol Biol. Oct. 11, 1996;262(5):732-45.

MacDonald et al., J Exp Med Apr. 1, 1988; 167(4):1341-9.

Mateo C, et al., "Removal of amphipathic epitopes from genetically engineered antibodies: production of modified immunoglobulins with reduced immunogenicity," Hybridoma. Dec. 2000;19(6):463-71.

Meadows et al, J. Interferon Res. 10(Suppl. 1):S159 (1990).

Meadows et al, Proc. Am. Assoc. Cancer Res. 31:55 (1990).

Merck Manual of Diagnosis and Therapy, Mark Beers and Robert Berkow, eds.,., Published by Merck Research Laboratories, 17th ed., 1999, 302-13.

Mitoro A, et al., "Exacerbation of ulcerative colitis during alpha-interferon therapy for chronic hepatitis C," *Intern Med.* (1993), 32(4):327-31.

Mogensen, et al., "The Type I Interferon Receptor: Structure, Function and Evolution of a Family Business," *J. of Interferon and Cytokine Research* (1999); 19: 1069-1098.

Monteleone G, et al., "Interferon-alpha drives T cell-mediated immunopathology in the intestine," Eur J Immunol. Aug. 2001;31(8):2247-55.

Monteleone G, et al., "Role of interferon alpha in promoting T helper cell type 1 responses in the small intestine in coeliac disease," *Gut.* (2001), 48(3):425-9.

Mouchel-Vielh et al, FEBS 313(3):255-259 (1992).

Paul, Fundamental Immunology, 3rd Ed., pp. 292-295, Raven Press, New York, 1993.

Radvanyi LG, et al., "Low levels of interferon-alpha induce CD86 (B7.2) expression and accelerates dendritic cell maturation from human peripheral blood mononuclear cells," Scand J Immunol. Nov. 1999;50(5):499-509.

Rampton DS, and Phil D, "New treatments for inflammatory bowel disease," World J Gastroenterol. Oct. 1998;4(5):369-376.

Raziuddin et al, Proceedings National Academy Science, vol. 81, Sep. 1984, "Receptors for human alpha and beta interferon but not for gamma interferon are specified by human chromosome 21", pp. 5504-5508.

Reff ME and Heard C, "A review of modifications to recombinant antibodies: attempt to increase efficacy in oncology applications," Crit Rev Oncol Hematol. Oct. 2001;40(1):25-35.

Revel et al, ICSU Short Reports, vol. 4, 1986 "Interferon receptor and interferon-activated genes", pp. 362-365.

Riechmann et al., "Reshaping Human Antibodies for Therapy", vol. 332, Mar. 25, 1988, pp. 323-327.

Rudikoff S, et al., "Single amino acid substitution altering antigen-binding specificity," Proc Natl Acad Sci U S A. Mar. 1982;79(6):1979-83.

Schellekens H, et al., "Factors inhibiting IFN activity," Biotherapy. 1996;8(3-4):199-204.

Shearer et al, J. Cell. Biochem. Supple. (12 Part A):216 (1988).

Siemers, Pro. Am. Assoc. Cancer Res. 31:238 (1990).

Sollid et al., J Exp Med. Jan. 1, 1989; 169(1):345-50.

Shulman et al, J. Interferon Res. 8(1) (1988) "Molecular cloning of the human IFN-alpha, beta receptor cDNA", p. S16, abstract No. 3-9.

Stewart TA, "Neutralizing interferon alpha as a therapeutic approach to autoimmune diseases," Cytokine Growth Factor Rev. Apr. 2003;14(2):139-54.

Tanaguchi et al., Curr Opon Immunol. Feb. 2002; 14(1):111-6.

Tilg H, et al., "Interferon-alpha induces circulating tumor necrosis factor receptor p55 in humans," Blood. Jan. 15, 1995;85(2):433-5.

Tough DF, et al., "Induction of bystander T cell proliferation by viruses and type I interferon in vivo," Science. Jun. 28, 1996;272(5270):1947-50.

Traub et al, J. Biol. Chem. 259(22):13872-77 (1984).

Uze et al., Proc. Natl. Acad. Sci, 89, 4774-4778, May 1992.

Vajdos FF, et al., "Comprehensive functional maps of the antigen-binding site of an anti-ErbB2 antibody obtained with shotgun scanning mutagenesis," J Mol Biol. Jul. 5, 2002;320(2):415-28.

Waldmann, Thomas A., Science, 252:1657-1662, Jun. 1991.

Wu H, et al., "Humanization of a murine monoclonal antibody by simultaneous optimization of framework and CDR residues," J Mol Biol. Nov. 19, 1999;294(1):151-62.

Yonehara et al., "Monoclonal Anti-Idiotype Antibody for Anti-Human Interferon-.alpha. that complete with Interferon.alpha. in Binding to Human Cell Surface and Inhibit the Interferon Action", Elsevier Sci. Publ. BV, (1986), pp. 167-171.

Non-Final Rejection mailed on Jun. 1, 2009 for U.S. Appl. No. 10/831,432.

Examiner interview Summary mailed on Jul. 6, 2009 for U.S. Appl. No. 10/831,432.

Uzé et al., Murine Tumor Cells Expressing the Gene for the Human Interferon αβ Receptor Elicit Antibodies in Syngeneic Mice to the Active Form of the Receptor., Eur. J. Immunol 1991, 21:447-451.

* cited by examiner

Anti-IFNAR 3F11 VH

V segment:      4-34
    D segment:      undetermined
    J segment:      JH6b

```
          Q   V   Q   L   Q   Q   W   G   A   G   L   L   K   P   S   E   T   L
   1     CAG GTG CAG CTA CAG CAG TGG GGC GCA GGA CTG TTG AAG CCT TCT GAG ACC CTG
                                                                       CDR1
                                                                       ~~~~~~~~~~~~~~~~~~~
          S   L   T   C   A   V   Y   G   G   S   F   S   G   Y   F   W   S   W
   55    TCC CTC ACC TGC GCT GTC TAT GGT GGG TCC TTC AGT GGT TAT TTC TGG AGC TGG
                                                                       CDR2
                                                                       ~~~~~~~~~~~~~~~~~~~
          I   R   Q   P   P   G   K   G   L   E   W   I   G   E   I   D   H   S
   109   ATC CGC CAG CCC CCA GGG AAG GGG CTG GAG TGG ATT GGG GAA ATC GAT CAC AGT
                      CDR2
          ~~~~~~~~~~~~~~~~~~~~~~~~~~~~~~~~~~~~~~~~~~~~
          G   K   T   N   Y   N   P   S   L   K   S   R   V   T   I   S   V   D
   163   GGA AAG ACC AAC TAC AAT CCG TCC CTC AAG AGT CGA GTT ACC ATA TCA GTA GAC

T   S   K   N   Q   V   S   L   K   L   S   S   V   T   A   A   D   T
   217   ACG TCC AAG AAC CAG GTC TCC CTG AAG CTG AGC TCT GTG ACC GCC GCG GAC ACG
                                                                 CDR3
                                                                 ~~~~~~~~~~~~~~~~~~~~~~~~~~~~~~~~~~~
          A   V   Y   Y   C   A   R   E   S   K   Y   Y   F   G   L   D   V   W
   271   GCT GTG TAT TAC TGT GCG AGA GAA AGC AAG TAC TAC TTC GGT TTG GAC GTC TGG

G   Q   G   T   T   V   T   V   T   S
   325   GGC CAA GGG ACC ACG GTC ACC GTC ACC TCA
```

Figure 1A

Anti-IFNAR 3F11 VK

```
V segment:    L18
J segment:    JK5
```

```
          A   I   Q   L   T   Q   S   P   S   S   L   S   A   S   V   G   D   R
  1       GCC ATC CAG TTG ACC CAG TCT CCA TCC TCC CTG TCT GCA TCT GTA GGA GAC AGA

CDR1
                                  ~~~~~~~~~~~~~~~~~~~~~~~~~~~~~~~~~~~~~~~~~~~~~~
          V   T   I   T   C   R   A   S   Q   G   I   Y   S   V   L   A   W   Y
 55       GTC ACC ATC ACT TGC CGG GCA AGT CAG GGC ATT TAC AGT GTT TTA GCC TGG TAT

CDR2
                                                        ~~~~~~~~~~~~~~~~~~~~~~~~
          Q   Q   K   P   G   K   T   P   K   L   L   I   Y   D   A   S   R   L
109       CAG CAG AAA CCA GGG AAA ACT CCT AAG CTC CTG ATC TAT GAT GCC TCC CGT TTG

CDR2
          ~~~~~~~~
          E   S   G   V   P   S   R   F   S   G   S   G   S   G   T   D   F   T
163       GAA AGT GGG GTC CCA TCA AGG TTC AGC GGC AGT GGA TCT GGG ACA GAT TTC ACT

CDR3
                                                                        ~~~~~~~~
          L   T   I   S   S   L   Q   P   E   D   F   A   T   Y   Y   C   Q   Q
217       CTC ACC ATC AGC AGC CTG CAG CCT GAA GAT TTT GCA ACT TAT TAC TGT CAA CAG

CDR3
          ~~~~~~~~~~~~~~~~~~~~~~~~~~
          F   N   S   Y   I   T   F   G   Q   G   T   R   L   E   I   K
271       TTT AAT AGT TAC ATC ACC TTC GGC CAA GGG ACA CGA CTG GAG ATT AAA
```

Figure 1B

Anti-IFNAR 4G5 VH

V segment: 4-34
        D segment: undetermined
        J segment: JH4b

```
         Q   V   Q   L   Q   Q   W   G   A   G   L   L   K   P   S   E   T   L
  1     CAG GTG CAG CTA CAG CAG TGG GGC GCA GGA CTG TTG AAG CCT TCG GAG ACC CTG

CDR1
                                                    ~~~~~~~~~~~~~~~~~~~~
         S   L   T   C   A   V   Y   G   G   S   F   S   N   Y   Y   W   S   W
 55     TCC CTC ACC TGC GCT GTC TAT GGT GGG TCC TTC AGT AAT TAC TAC TGG AGC TGG

CDR2
                                                            ~~~~~~~~~~~~~~~~~~~~
         I   R   Q   P   P   G   K   G   L   E   W   I   G   E   I   I   L   S
109     ATC CGC CAG CCC CCA GGG AAG GGG CTG GAG TGG ATT GGG GAA ATC ATT CTT AGT

CDR2
       ~~~~~~~~~~~~~~~~~~~~~~~~~~~~~~~~~~~~~~~~~~~~~
         G   S   T   N   Y   N   P   S   L   K   S   R   V   T   I   S   V   D
163     GGA AGC ACC AAC TAC AAC CCG TCC CTC AAG AGT CGA GTC ACC ATA TCA GTA GAC

T   S   K   N   Q   F   S   L   N   L   T   S   V   T   A   A   D   T
217     ACG TCC AAG AAC CAG TTC TCC CTG AAC CTG ACC TCT GTG ACC GCC GCG GAC ACG

CDR3
                                            ~~~~~~~~~~~~~~~~~~~~~~~~~~~~~~~~~~~~~
         A   V   Y   Y   C   A   R   E   S   K   W   G   Y   Y   F   D   S   W
271     GCT GTG TAT TAC TGT GCG AGA GAG TCT AAA TGG GGT TAC TAC TTT GAC TCC TGG

G   Q   G   T   L   V   T   V   S   S
325     GGC CAG GGA ACC CTG GTC ACC GTC TCC TCA
```

Figure 2A

Anti-IFNAR 4G5 VK

V segment: L18
    J segment: JK2

```
        A   I   Q   L   T   Q   S   P   S   S   L   S   A   S   V   G   D   R
  1    GCC ATC CAG TTG ACC CAG TCT CCA TCC TCC CTG TCT GCA TCT GTA GGA GAC AGA

CDR1
                                        ~~~~~~~~~~~~~~~~~~~~~~~~~~~~~~~~~~~~~~
        V   T   I   T   C   R   A   T   Q   D   I   S   I   A   L   V   W   Y
 55    GTC ACC ATC ACT TGC CGG GCA ACT CAG GAC ATT AGC ATT GCT TTA GTC TGG TAT

CDR2
                                                ~~~~~~~~~~~~~~~~~~~~~~~~~~~~~~
        Q   Q   K   P   G   K   A   P   E   L   L   I   Y   D   A   S   G   L
109    CAG CAG AAA CCA GGG AAA GCT CCT GAG CTC CTG ATC TAT GAT GCC TCC GGT TTG

CDR2
       ~~~~~~~
        G   S   G   V   P   S   R   F   S   G   S   G   S   G   T   D   F   T
163    GGA AGT GGG GTC CCA TCA AGG TTC AGC GGC AGT GGA TCT GGC ACA GAT TTC ACT

CDR3
                                                                       ~~~~~~~
        L   T   I   S   S   L   Q   P   E   D   F   A   T   Y   Y   C   Q   Q
217    CTC ACC ATC AGC AGC CTG CAG CCT GAA GAT TTT GCA ACT TAT TAC TGT CAA CAG

CDR3
       ~~~~~~~~~~~~~~~~~~~~~~~~~~~~~~~
        F   N   S   Y   P   Y   T   F   G   Q   G   T   K   L   E   I   K
271    TTT AAT AGT TAC CCG TAC ACT TTT GGC CAG GGG ACC AAG CTG GAG ATC AAA
```

Figure 2B

Anti-IFNAR 11E2 VH

V segment: 5-51
    D segment: undetermined
    J segment: JH4b

```
        E   V   Q   L   V   Q   S   G   A   E   V   K   K   P   G   E   S   L
  1     GAG GTG CAG CTG GTG CAG TCT GGA GCA GAG GTG AAA AAG CCC GGG GAG TCT CTG

CDR1
                                                            ~~~~~~~~~~~~~~~~~~~
        K   I   S   C   K   G   S   G   Y   I   F   T   N   Y   W   I   A   W
 55     AAG ATC TCC TGT AAG GGT TCT GGA TAC ATC TTT ACC AAT TAC TGG ATC GCC TGG

CDR2
                                                                ~~~~~~~~~~~~~~~
        V   R   Q   M   P   G   K   G   L   E   S   M   G   I   I   Y   P   G
109     GTG CGC CAG ATG CCC GGT AAA GGC CTG GAG TCG ATG GGG ATC ATC TAT CCT GGT

CDR2
        ~~~~~~~~~~~~~~~~~~~~~~~~~~~~~~~~~~~~~~~~~~~~~~~
        D   S   D   I   R   Y   S   P   S   F   Q   G   Q   V   T   I   S   A
163     GAC TCT GAT ATC AGA TAC AGC CCG TCC TTC CAA GGC CAG GTC ACC ATC TCA GCC

D   K   S   I   T   T   A   Y   L   Q   W   S   S   L   K   A   S   D
217     GAC AAG TCC ATC ACC ACC GCC TAC CTG CAG TGG AGC AGT CTG AAG GCC TCA GAC

CDR3
                                            ~~~~~~~~~~~~~~~~~~~~~~~~~~~~~~~~~~~
        T   A   M   Y   Y   C   A   R   H   D   I   E   G   F   D   Y   W   G
271     ACC GCC ATG TAT TAC TGT GCG AGA CAT GAC ATA GAG GGG TTT GAC TAC TGG GGC

R   G   T   L   V   T   V   S   S
325     CGG GGA ACC CTG GTC ACC GTC TCC TCA
```

Figure 3A

Anti-IFNAR 11E2 VK

V segment: A27
        J segment: JK5

```
          E   I   V   L   T   Q   S   P   G   T   L   S   L   S   P   G   E   R
  1      GAA ATT GTG TTG ACG CAG TCT CCA GGC ACC CTG TCT TTG TCT CCA GGG GAA AGA
                                                                   CDR1
                                                          ~~~~~~~~~~~~~~~~~~~~~~~~~~~~~~~~~~~~~~~~~~~~~~~~~~
          A   T   L   S   C   R   A   S   Q   S   V   S   S   S   F   F   A   W
 55      GCC ACC CTC TCC TGC AGG GCC AGT CAG AGT GTT AGC AGC AGC TTC TTC GCC TGG
                                                                       CDR2
                                                                ~~~~~~~~~~~~~~~~~
          Y   Q   Q   K   P   G   Q   A   P   R   L   L   I   Y   G   A   S   S
109      TAC CAG CAG AAA CCT GGC CAG GCT CCC AGG CTC CTC ATC TAT GGT GCA TCC AGC
             CDR2
         ~~~~~~~~~~~~
          R   A   T   G   I   P   D   R   L   S   G   S   G   S   G   T   D   F
163      AGG GCC ACT GGC ATC CCA GAC AGG TTA AGT GGC AGT GGG TCT GGG ACA GAC TTC
                                                                           CDR3
                                                                           ~~~
          T   L   T   I   T   R   L   E   P   E   D   F   A   V   Y   Y   C   Q
217      ACT CTC ACC ATC ACC AGA CTG GAG CCT GAA GAT TTT GCA GTG TAT TAC TGT CAG
                 CDR3
         ~~~~~~~~~~~~~~~~~~~~~~~~~~~~~~~~~~
          Q   Y   D   S   S   A   I   T   F   G   Q   G   T   R   L   E   I   K
271      CAG TAT GAT AGC TCA GCG ATC ACC TTC GGC CAA GGG ACA CGA CTG GAG ATT AAA
```

Figure 3B

Anti-IFNAR 9D4 VH

V segment: 5-51
        D segment: undetermined
        J segment: JH4b

```
          E    V    Q    L    V    Q    S    G    A    E    V    K    K    P    G    E    S    L
  1       GAG  GTG  CAG  CTG  GTG  CAG  TCT  GGA  GCA  GAG  GTG  AAA  AAG  CCC  GGG  GAG  TCT  CTG

CDR1
                                                                       ~~~~~~~~~~~~~~~~~~~
          K    I    S    C    K    G    S    G    Y    I    F    T    N    Y    W    I    A    W
 55       AAG  ATC  TCC  TGT  AAG  GGT  TCT  GGA  TAC  ATC  TTT  ACC  AAC  TAC  TGG  ATC  GCC  TGG

CDR2
                                                                       ~~~~~~~~~~~~~~~~~~~
          V    R    Q    M    P    G    K    G    L    E    S    M    G    I    I    Y    P    G
109       GTG  CGC  CAG  ATG  CCC  GGT  AAA  GGC  CTG  GAG  TCG  ATG  GGG  ATC  ATC  TAT  CCT  GGT

CDR2
          ~~~~~~~~~~~~~~~~~~~~~~~~~~~~~~~~~~~~~~~~~~~~~~~~~~~~~~~
          D    S    D    I    R    Y    S    P    S    F    Q    G    Q    V    T    I    S    A
163       GAC  TCT  GAT  ATC  AGA  TAC  AGC  CCG  TCC  TTC  CAA  GGC  CAG  GTC  ACC  ATC  TCA  GCC

D    K    S    I    T    T    A    Y    L    Q    W    S    S    L    K    A    S    D
217       GAC  AAG  TCC  ATC  ACC  ACC  GCC  TAC  CTG  CAG  TGG  AGC  AGT  CTG  AAG  GCC  TCA  GAC

CDR3
                                                          ~~~~~~~~~~~~~~~~~~~~~~~~~~~~~~~~~~
          T    A    M    Y    Y    C    A    R    H    D    I    E    G    F    D    Y    W    G
271       ACC  GCC  ATG  TAT  TAC  TGT  GCG  AGA  CAT  GAC  ATA  GAG  GGG  TTT  GAC  TAC  TGG  GGC

R    G    T    L    V    T    V    S    S
325       CGG  GGA  ACC  CTG  GTC  ACC  GTC  TCC  TCA
```

Figure 4A

Anti-IFNAR 9D4 VK

V segment: A27
    J segment: JK5

```
        E   I   V   L   T   Q   S   P   G   T   L   S   L   S   P   G   E   R
  1    GAA ATT GTG TTG ACG CAG TCT CCA GGC ACC CTG TCT TTG TCT CCA GGG GAA AGA

CDR1
                                         ~~~~~~~~~~~~~~~~~~~~~~~~~~~~~~~~~~~~~~~~~~
        A   T   L   S   C   R   A   S   Q   S   V   S   S   S   F   F   A   W
 55    GCC ACC CTC TCC TGC AGG GCC AGT CAG AGT GTT AGC AGC AGC TTC TTC GCC TGG

CDR2
                                                              ~~~~~~~~~~~~~~~~~
        Y   Q   Q   K   P   G   Q   A   P   R   L   L   I   Y   G   A   S   S
109    TAC CAG CAG AAA CCT GGC CAG GCT CCC AGG CTC CTC ATC TAT GGT GCA TCC AGC

CDR2
        ~~~~~~~~~~~~
        R   A   T   G   I   P   D   R   L   S   G   S   G   S   G   T   D   F
163    AGG GCC ACT GGC ATC CCA GAC AGG TTA AGT GGC AGT GGG TCT GGG ACA GAC TTC

CDR3
                                                                         ~~~
        T   L   T   I   T   R   L   E   P   E   D   F   A   V   Y   Y   C   Q
217    ACT CTC ACC ATC ACC AGA CTG GAG CCT GAA GAT TTT GCA GTG TAT TAC TGT CAG

CDR3
        ~~~~~~~~~~~~~~~~~~~~~~~~~~~~~~
        Q   Y   D   S   S   A   I   T   F   G   Q   G   T   R   L   E   I   K
271    CAG TAT GAT AGC TCA GCG ATC ACC TTC GGC CAA GGG ACA CGA CTG GAG ATT AAA
```

Figure 4B

Anti-IFNAR 3F11 VH Region

```
     CDR1
4-34 Germline:    Q V Q L Q Q W G A G L L K P S E T L S L T C A V Y G G
S F S G Y Y W S W I R Q P
3F11 VH:          - - - - - - - - - - - - - - - - - - - - - - - - - -
- - - - - F - - - - - - -

CDR2
4-34 Germline:    P G K G L E W I G E I N H S G S T N Y N P S L K S R V
T I S V D T S K N Q F S L
3F11 VH:          - - - - - - - - - - D - - - K - - - - - - - - - - -
- - - - - - - - - - V - -

CDR3
4-34 Germline:    K L S S V T A A D T A V Y Y C A R
3F11 VH:          - - - - - - - - - - - - - - - - - E S K Y Y F G L D V
W G Q G T T V T V T S
```

Figure 5

Anti-IFNAR 4G5 VH region

```
                                                              ___CDR1___
4-34 Germline:  Q V Q L Q Q W G A G L L K P S E T L S L T C A V Y G G
S F S G Y Y W S W I R Q P
4G5 VH:         - - - - - - - - - - - - - - - - - - - - - - - - - - -
- - - N - - - - - - - -
```

```
                                            _____CDR2_____
4-34 Germline:  P G K G L E W I G E I N H S G S T N Y N P S L K S R V
T I S V D T S K N Q F S L
4G5 VH:         - - - - - - - - - - I L - - - - - - - - - - - - - -
- - - - - - - - - - - - -
```

```
                                                          _____CDR3_____
4-34 Germline:  K L S S V T A A D T A V Y Y C A R
4G5 VH:         N - T - - - - - - - - - - - - - - E S K W G Y Y F D S
W G Q G T L V T V S S
```

Figure 6

Anti-IFNAR 11E2 and 9D4 VH regions

```
                                                                          ___CDR1___
5-51 Germline:  E V Q L V Q S G A E V K K P G E S L K I S C K G S G Y
S F T S Y W I G W V R Q M P
11E2 VH:        - - - - - - - - - - - - - - - - - - - - - - - - - -
I - - N - - - A - - - - - -
9D4 VH:         - - - - - - - - - - - - - - - - - - - - - - - - - -
I - - N - - - A - - - - - -

_____CDR2_____
5-51 Germline:  G K G L E W M G I I Y P G D S D T R Y S P S F Q G Q V
T I S A D K S I S T A Y L Q
11E2 VH:        - - - - - S - - - - - - - - - - I - - - - - - - - - -
- - - - - - - - T - - - - -
9D4 VH:         - - - - - S - - - - - - - - - - I - - - - - - - - - -
- - - - - - - - T - - - - -

_____CDR3_____
5-51 Germline:  W S S L K A S D T A M Y Y C A R
11E2 VH:        - - - - - - - - - - - - - - - - H D I E G F D Y W G R
G T L V T V S S
9D4 VH:         - - - - - - - - - - - - - - - - - - - - - - - - - -
- - - - - - - -
```

Figure 7

Anti-IFNAR 3F11 VK Region

```
             _____CDR1_____
L18 Germline:  A I Q L T Q S P S S L S A S V G D R V T I T C R A
S Q G I S S A L A W Y
3F11 VK:       - - - - - - - - - - - - - - - - - - - - - - - -
- - - - Y - V - - - -

_____CDR2_____
L18 Germline:  Q Q K P G K A P K L L I Y D A S S L E S G V P S R
F S G S G S G T D F T
3F11 VK:       - - - - - - T - - - - - - - - - R - - - - - - -
- - - - - - - - - - -

_____CDR3_____
L18 Germline:  L T I S S L Q P E D F A T Y Y C Q Q F N S Y P
3F11 VK:       - - - - - - - - - - - - - - - - - - - - - I T F
G Q G T R L E I K
```

Figure 8

Anti-IFNAR 4G5 VK region

```
                                                            CDR1
L18 Germline:   A I Q L T Q S P S S L S A S V G D R V T I T C R A S Q
                G I S S A L A W Y Q Q K P
4G5 VK:         - - - - - - - - - - - - - - - - - - - - - - - T -
                D - - I - - V - - - - - -

CDR2
L18 Germline:   G K A P K L L I Y D A S S L E S G V P S R F S G S G S
                G T D F T L T I S S L Q P
4G5 VK:         - - - - E - - - - - - - G - G - - - - - - - - - - - -
                - - - - - - - - - - - - -

CDR3
L18 Germline:   E D F A T Y Y C Q Q F N S Y P
4G5 VK:         - - - - - - - - - - - - - - - Y T F G Q G T K L E I K
```

Figure 9

Anti-IFNAR 11E2 and 9D4 VK regions

```
                                              _____CDR1_____
A27 Germline:     E I V L T Q S P G T L S L S P G E R A T L S C R A S Q
S V S S S Y L A W Y Q Q K P
11E2 VK:          - - - - - - - - - - - - - - - - - - - - - - - - - -
- - - - - F F - - - - - - -
9D4 VK:           - - - - - - - - - - - - - - - - - - - - - - - - - -
- - - - - F F - - - - - - -

_____CDR2_____
A27 Germline:     G Q A P R L L I Y G A S S R A T G I P D R F S G S G S
          G T D F T L T I S R L E P E
11E2 VK:          - - - - - - - - - - - - - - - - - - - - - L - - - - -
          - - - - - - - T - - - - -
9D4 VK:           - - - - - - - - - - - - - - - - - - - - - L - - - - -
          - - - - - - - T - - - - -

_____CDR3_____
A27 Germline:     D F A V Y Y C Q Q Y G S S P
11E2 VK:          - - - - - - - - - - D - - A I T F G Q G T R L E I K
9D4 VK:           - - - - - - - - - - D - - A - - - - - - - - - - -
```

INTERFERON ALPHA RECEPTOR 1 ANTIBODIES AND THEIR USES

This application claims priority to U.S. provisional application No. 60/581,747, filed Jun. 21, 2004; the contents of which are hereby incorporated by reference in their entirety.

BACKGROUND OF THE INVENTION

Type I interferons (IFN) (IFN-α, IFN-β, IFN-ω, IFN-Y) are a family of structurally related cytokines having antiviral, antitumor and immunomodulatory effects (Hardy et al. (2001) *Blood* 97:473; Cutrone and Langer (2001) *J. Biol. Chem.* 276:17140). The human IFNα locus includes two subfamilies. The first subfamily consists of 14 non allelic genes and 4 pseudogenes having at least 80% homology. The second subfamily, αII or omega (ω), contains 5 pseudogenes and 1 functional gene which exhibits 70% homology with the IFNα genes (Weissmann and Weber (1986) *Prog. Nucl. Acid Res. Mol. Biol.*, 33:251-300). The subtypes of IFNα have different specific activities but they possess the same biological spectrum (Streuli et al. (1981) *Proc. Natl. Acad. Sci. USA* 78:2848) and have the same cellular receptor (Agnet M. et al. in "Interferon 5" Ed. I. Gresser p. 1-22, Academic Press, London 1983).

The interferon β (IFNβ) is encoded by a single gene which has approximately 50% homology with the IFNα genes.

Gamma interferon, which is produced by activated lymphocytes, does not possess any homology with the alpha/beta interferons and it does not react with their receptor.

All human type I interferons bind to a cell surface receptor (IFN alpha receptor, IFNAR) consisting of two transmembrane proteins, IFNAR-1 and IFNAR-2 (Uze et. al. (1990) *Cell* 60:225; Novick et al. (1994) *Cell* 77:391). IFNAR-1 is essential for high affinity binding and differential specificity of the IFNAR complex (Cutrone, 2001, supra). While functional differences for each of the type I IFN subtypes have not been identified it is thought that each may exhibit different interactions with the IFNAR receptor components leading to potentially diverse signaling outcomes (Cook et al. (1996) *J. Biol. Chem.* 271:13448). In particular, studies utilizing mutant forms of IFNAR1 and IFNAR2 suggested that alpha and beta interferons signal differently through the receptor by interacting differentially with respective chains (Lewerenz et al. (1998) *J. Mol. Biol.* 282:585).

Early functional studies of type I IFNs focused on innate defense against viral infections (Haller et al. (1981) *J. Exp. Med.* 154:199; Lindenmann et al. (1981) *Methods Enzymol.* 78:181). More recent studies, however, implicate type I IFNs as potent immunoregulatory cytokines in the adaptive immune response. Specifically, type I IFNs have been shown to facilitate differentiation of naive T cells along the Th1 pathway (Brinkmann et al. (1993) *J Exp. Med.* 178:1655), to enhance antibody production (Finkelman et al. (1991) *J. Exp. Med.* 174:1179) and to support the functional activity and survival of memory T cells (Santini et al. (2000) *J Exp. Med.* 191:1777; Tough et al. (1996) *Science* 272:1947).

Recent work by a number of groups suggests that IFN-α may enhance the maturation or activation of dendritic cells (DCs) (Santini, et al. (2000) *J. Exp. Med.* 191:1777; Luft et al. (1998) *J. Immunol.* 161:1947; Luft et al. (2002) *Int. Immunol.* 14:367; Radvanyi et al. (1999) *Scand. J. Immunol.* 50:499). Furthermore, increased expression of type I interferons has been described in numerous autoimmune diseases (Foulis et al. (1987) *Lancet* 2:1423; Hooks et al. (1982) *Arthritis Rheum.* 25:396; Hertzog et al. (1988) *Clin. Immunol. Immunopathol.* 48:192; Hopkins and Meager (1988) *Clin. Exp. Immunol.* 73:88; Arvin and Miller (1984) *Arthritis Rheum.* 27:582). The most studied examples of this are insulin-dependent diabetes mellitus (IDDM) (Foulis (1987) supra) and systemic lupus erythematosus (SLE) (Hooks (1982) supra), which are associated with elevated levels of IFN-α, and rheumatoid arthritis (RA) (Hertzog (1988), Hopkins and Meager (1988), Arvin and Miller (1984), supra) in which IFN-β may play a more significant role.

Moreover, administration of interferon α has been reported to exacerbate underlying disease in patients with psoriasis and multiple sclerosis and to induce an SLE like syndrome in patients without a previous history of autoimmune disease. Interferon α has also been shown to induce glomerulonephritis in normal mice and to accelerate the onset of the spontaneous autoimmune disease of NZB/W mice. Further, IFN-α therapy has been shown in some cases to lead to undesired side effects, including fever and neurological disorders. Hence there are pathological situations in which inhibition of Type I IFN activity may be beneficial to the patient and a need exists for agents effective in inhibiting Type I IFN activity.

SUMMARY OF THE INVENTION

The present invention provides isolated human monoclonal antibodies that bind to IFNAR-1 and inhibit the biological activity of type I interferon, preferably multiple type I interferons. Furthermore, the antibodies do not bind to the same epitope as the murine anti-IFNAR-1 antibody, 64G12.

In one aspect, the invention pertains to an isolated human antibody, or antigen binding portion thereof, wherein the antibody specifically binds to IFNAR-1 and exhibits one or more of the following properties:

a) binds to IFNAR-1 with a $K_D$ of $1 \times 10^{-7}$ M or greater affinity;
b) inhibits the biological activity of multiple Type I interferons;
c) inhibits the activity of IFN α 2b in a Daudi cell proliferation assay;
d) inhibits the activity of IFN omega in a Daudi cell proliferation assay;
e) inhibits IP-10 secretion by peripheral blood mononuclear cells induced by IFN α 2b;
f) inhibits IP-10 secretion by peripheral blood mononuclear cells induced by IFN omega;
g) inhibits dendritic cell development mediated by Systemic Lupus Erythematosus plasma; and
h) binds to a different epitope than murine monoclonal antibody 64G12 (ECACC Deposit No. 92022605).

Preferred antibodies of the invention specifically bind to human interferon alpha receptor 1 and bind with a $K_D$ of $1 \times 10^{-8}$ M or greater affinity, or $1 \times 10^{-9}$ M or greater affinity, or $5 \times 10^{-10}$ M or greater affinity or $2 \times 10^{-10}$ M or greater affinity In one aspect, the invention pertains to an isolated monoclonal antibody, or an antigen-binding portion thereof, comprising a heavy chain variable region that is the product of or derived from a human $V_H$ 4-34 or 5-51 gene, wherein the antibody specifically binds to human interferon alpha receptor 1. In another aspect, the invention pertains to an isolated monoclonal antibody, or an antigen-binding portion thereof, comprising a light chain variable region that is the product of or derived from a human $V_K$ L18 or A27 gene, wherein the antibody specifically binds to human interferon alpha receptor 1. In yet another aspect, the invention pertains to an isolated human monoclonal antibody, or antigen-binding portion thereof, comprising:

(a) a heavy chain variable region that is the product of or derived from a human $V_H$ 4-34 or 5-51 gene; and (b) a light chain variable region that is the product of or derived from a human Vk L18 or A27 gene;

wherein the antibody specifically binds to human interferon alpha receptor 1. In preferred embodiments, the antibody comprises a heavy chain variable region of a human $V_H$ 4-34 gene and a light chain variable region of a human $V_K$ L18 gene or the antibody comprises a heavy chain variable region of a human $V_H$ 5-51 gene and a light chain variable region of a human $V_K$ A27 gene.

In another aspect, the invention provides an isolated human monoclonal antibody, or antigen-binding portion thereof, comprising:

a human heavy chain variable region comprising CDR1, CDR2, and CDR3 sequences; and a human light chain variable region comprising CDR1, CDR2, and CDR3 sequences, wherein:

(a) the human heavy chain variable region CDR3 sequence comprises an amino acid sequence selected from the group consisting of amino acid sequences of SEQ ID NO: 9, 10, 11, and 12, and conservative modifications thereof;

(b) the human light chain variable region CDR3 sequence comprises an amino acid sequence selected from the group consisting of amino acid sequence of SEQ ID NO:21, 22, 23, and 24, and conservative modifications thereof;

(c) the antibody specifically binds human interferon alpha receptor 1 with a binding affinity of at least $1\times10^{-8}$ M or greater affinity; and (d) the antibody inhibits the biological activity of at least one Type I interferon.

Preferably, the human heavy chain variable region CDR2 sequence comprises an amino acid sequence selected from the group consisting of amino acid sequences of SEQ ID NO: 5, 6, 7, and 8, and conservative modifications thereof; and the human light chain variable region CDR2 sequence comprises an amino acid sequence selected from the group consisting of amino acid sequences of SEQ ID NO: 17, 18, 19, and 20, and conservative modifications thereof. Preferably, the human heavy chain variable region CDR1 sequence comprises an amino acid sequence selected from the group consisting of amino acid sequences of SEQ ID NO: 1, 2, 3, and 4, and conservative modifications thereof; and the human light chain variable region CDR1 sequence comprises an amino acid sequence selected from the group consisting of amino acid sequences of SEQ ID NO: 13, 14, 15, and 16, and conservative modifications thereof.

In another aspect, the invention pertains to an isolated human monoclonal antibody, or antigen-binding portion thereof, comprising a human heavy chain variable region and a human light chain variable region, wherein:

(a) the human heavy chain variable region comprises an amino acid sequence that is at least 80% homologous to an amino acid sequence selected from the group consisting of SEQ ID NO: 25, 26, 27, and 28;

(b) the human light chain variable region comprises an amino acid sequence that is at least 80% homologous to an amino acid sequence selected from the group consisting of SEQ ID NO: 29, 30, 31, and 32;

(c) the antibody specifically binds human interferon alpha receptor 1 with a binding affinity of at least $1\times10^{-8}$ M or greater affinity; and (d) the antibody inhibits the biological activity of at least one Type I interferon.

Preferred antibodies of the invention include isolated human monoclonal antibodies, or antigen-binding portions thereof, comprising:

(a) a human heavy chain variable region CDR1 comprising an amino acid sequence selected from the group consisting of SEQ ID NOs: 1, 2, 3, and 4;

(b) a human heavy chain variable region CDR2 comprising an amino acid sequence selected from the group consisting of SEQ ID NOs: 5, 6, 7, and 8;

(c) a human heavy chain variable region CDR3 comprising an amino acid sequence selected from the group consisting of SEQ ID NOs: 9, 10, 11, and 12;

(d) a human light chain variable region CDR1 comprising an amino acid sequence selected from the group consisting of SEQ ID NOs: 13, 14, 15, and 16;

(e) a human light chain variable region CDR2 comprising an amino acid sequence selected from the group consisting of SEQ ID NOs: 17, 18, 19, and 20; and (f) a human light chain variable region CDR3 comprising an amino acid sequence selected from the group consisting of SEQ ID NOs: 21, 22, 23, and 24;

wherein the antibody specifically binds human interferon alpha receptor 1 with a binding affinity of at least $1\times10^{-8}$ M or greater affinity.

Preferred combinations of CDR regions include the following:

(a) a human heavy chain variable region CDR1 comprising SEQ ID NO:1;

(b) a human heavy chain variable region CDR2 comprising SEQ ID NO:5;

(c) a human heavy chain variable region CDR3 comprising SEQ ID NO:9;

(d) a human light chain variable region CDR1 comprising SEQ ID NO:13;

(e) a human light chain variable region CDR2 comprising SEQ ID NO:17; and (f) a human light chain variable region CDR3 comprising SEQ ID NO:21.

(a) a human heavy chain variable region CDR1 comprising SEQ ID NO:2;

(b) a human heavy chain variable region CDR2 comprising SEQ ID NO:6;

(c) a human heavy chain variable region CDR3 comprising SEQ ID NO:10;

(d) a human light chain variable region CDR1 comprising SEQ ID NO:14;

(e) a human light chain variable region CDR2 comprising SEQ ID NO:18; and (f) a human light chain variable region CDR3 comprising SEQ ID NO:22.

(a) a human heavy chain variable region CDR1 comprising SEQ ID NO:3;

(b) a human heavy chain variable region CDR2 comprising SEQ ID NO:7;

(c) a human heavy chain variable region CDR3 comprising SEQ ID NO:11;

(d) a human light chain variable region CDR1 comprising SEQ ID NO:15;

(e) a human light chain variable region CDR2 comprising SEQ ID NO:19; and (f) a human light chain variable region CDR3 comprising SEQ ID NO:23.

(a) a human heavy chain variable region CDR1 comprising SEQ ID NO:4;

(b) a human heavy chain variable region CDR2 comprising SEQ ID NO:8;

(c) a human heavy chain variable region CDR3 comprising SEQ ID NO:12;
(d) a human light chain variable region CDR1 comprising SEQ ID NO:16;
(e) a human light chain variable region CDR2 comprising SEQ ID NO:20; and
(f) a human light chain variable region CDR3 comprising SEQ ID NO:24.

Other preferred antibodies of the invention include isolated human monoclonal antibodies, or antigen binding portions thereof, comprising:
(a) a human heavy chain variable region comprising an amino acid sequence selected from the group consisting of SEQ ID NOs: 25, 26, 27, and 28; and
(b) a human light chain variable region comprising an amino acid sequence selected from the group consisting of SEQ ID NOs: 29, 30, 31, and 32;
wherein the antibody specifically binds human interferon alpha receptor 1 with a binding affinity of at least $1 \times 10^{-8}$ M or greater affinity.

Preferred combinations of heavy and light chains include the following:
(a) a human heavy chain variable region comprising the amino acid sequence of SEQ ID NO:25; and
(b) a human light chain variable region comprising the amino acid sequence of SEQ ID NO:29.
(a) a human heavy chain variable region comprising the amino acid sequence of SEQ ID NO:26; and
(b) a human light chain variable region comprising the amino acid sequence of SEQ ID NO:30.
(a) a human heavy chain variable region comprising the amino acid sequence of SEQ ID NO:27; and
(b) a human light chain variable region comprising the amino acid sequence of SEQ ID NO:31.
(a) a human heavy chain variable region comprising the amino acid sequence of SEQ ID NO:28; and
(b) a human light chain variable region comprising the amino acid sequence of SEQ ID NO:32.

Another aspect of the invention pertains to antibodies that compete for binding to IFNAR-1 with a reference antibody provided by the invention. Accordingly, in another embodiment, the invention provides:
an isolated monoclonal antibody, or antigen binding protion thereof, wherein the antibody cross-competes for binding to human interferon alpha receptor 1 with a reference antibody, wherein the reference antibody is selected from the group consisting of:
a) an antibody comprising a heavy chain variable region comprising the amino acid sequence of SEQ ID NO: 25; and a light chain variable region comprising the amino acid sequence of SEQ ID NO: 29;
b) an antibody comprising a heavy chain variable region comprising the amino acid sequence of SEQ ID NO: 26; and a light chain variable region comprising the amino acid sequence of SEQ ID NO: 30;
c) an antibody comprising a heavy chain variable region comprising the amino acid sequence of SEQ ID NO: 27; and a light chain variable region comprising the amino acid sequence of SEQ ID NO: 31; and
d) an antibody comprising a heavy chain variable region comprising the amino acid sequence of SEQ ID NO: 28; and a light chain variable region comprising the amino acid sequence of SEQ ID NO: 32.

In certain embodiments, the invention provides a human antibody, or antigen-binding portion thereof, wherein the antibody does not bind the same epitope as (i.e., does not cross-compete with) mouse monoclonal antibody 64G12 (ECACC Deposit No. 92022605).

The antibodies of the invention can be of any isotype. Preferred antibodies are of the IgG1, IgG3 or IgG4 isotype. The antibodies of the invention can be full-length antibodies comprising variable and constant regions, or they can be antigen-binding fragments thereof, such as a single chain antibody, or a Fab or Fab'2 fragment.

The invention also provides an immunoconjugate comprising an antibody of the invention, or antigen-binding portion thereof, linked to a therapeutic agent, such as a cytotoxin or a radioactive isotope. The invention also provides a bispecific molecule comprising an antibody, or antigen-binding portion thereof, of the invention, linked to a second functional moiety having a different binding specificity than said antibody, or antigen binding portion thereof.

Compositions comprising an antibody, or antigen-binding portion thereof, or immunoconjugate or bispecific molecule of the invention and a pharmaceutically acceptable carrier are also provided.

Nucleic acid molecules encoding the antibodies, or antigen-binding portions thereof, of the invention are also encompassed by the invention, as well as expression vectors comprising such nucleic acids and host cells comprising such expression vectors. Moreover, the invention provides a transgenic mouse comprising human immunoglobulin heavy and light chain transgenes, wherein the mouse expresses an antibody of the invention, as well as hybridomas prepared from such a mouse, wherein the hybridoma produces the antibody of the invention.

The invention also provides methods for making "second generation" anti-IFNAR-1 antibodies based on the sequences of the anti-IFNAR-1 antibodies provided herein. For example, the invention provides a method for preparing an anti-IFNAR-1 antibody comprising:
(a) providing: (i) a heavy chain variable region antibody sequence comprising a CDR1 sequence that is selected from the group consisting of SEQ ID NOs: 1, 2, 3 and 4, a CDR2 sequence that is selected from the group consisting of SEQ ID NOs: 5, 6, 7, and 8; and a CDR3 sequence that is selected from the group consisting of SEQ ID NOs: 9, 10, 11, and 12; or (ii) a light chain variable region antibody sequence comprising a CDR1 sequence that is selected from the group consisting of SEQ ID NOs: 13, 14, 15, and 16, a CDR2 sequence that is selected from the group consisting of SEQ ID NOs: 17, 18, 19, and 20 and a CDR3 sequence that is selected from the group consisting of SEQ ID NOs: 21, 22, 23, and 24;
(b) altering at least one amino acid residue within at least one variable region antibody sequence, said sequence being selected from the heavy chain variable region antibody sequence and the light chain variable region antibody sequence, to create at least one altered antibody sequence; and
(c) expressing the altered antibody sequence as a protein.

The invention also provides a method for inhibiting biological activity of a type I interferon on a cell expressing interferon alpha receptor 1 comprising contacting the cell with the antibody of the invention, such that the biological activity of the type I interferon is inhibited. The invention also provides a method of treating a type I interferon-mediated disease or disorder in a subject in need of treatment comprising administering to the subject the antibody, or antigen-binding portion thereof, of the invention, such that the type-I interferon mediated disease in the subject is treated. The type I interferon-mediated disease can be, for example, an interferon alpha-mediated disease.

Examples of disease or disorders that can be treated using the methods of the invention include systemic lupus erythematosus, insulin dependent diabetes mellitus, inflammatory bowel disease, multiple sclerosis, psoriasis, autoimmune thyroiditis, rheumatoid arthritis, glomerulonephritis, HIV infection, AIDS, transplant rejection and graft versus host disease.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO: 33) and amino acid sequence (SEQ ID NO: 25) of the heavy chain variable region of the 3F11 human monoclonal antibody. The CDR1 (SEQ ID NO: 1), CDR2 (SEQ ID NO: 5) and CDR3 (SEQ ID NO: 9) regions are delineated.

FIG. 1B shows the nucleotide sequence (SEQ ID NO: 37) and amino acid sequence (SEQ ID NO: 29) of the light chain variable region of the 3F11 human monoclonal antibody. The CDR1 (SEQ ID NO: 13), CDR2 (SEQ ID NO: 17) and CDR3 (SEQ ID NO: 21) regions are delineated.

FIG. 2A shows the nucleotide sequence (SEQ ID NO: 34) and amino acid sequence (SEQ ID NO: 26) of the heavy chain variable region of the 4G5 human monoclonal antibody. The CDR1 (SEQ ID NO: 2), CDR2 (SEQ ID NO: 6) and CDR3 (SEQ ID NO: 10) regions are delineated.

FIG. 2B shows the nucleotide sequence (SEQ ID NO: 38) and amino acid sequence (SEQ ID NO: 30) of the light chain variable region of the 4G5 human monoclonal antibody. The CDR1 (SEQ ID NO: 14), CDR2 (SEQ ID NO: 18) and CDR3 (SEQ ID NO: 22) regions are delineated.

FIG. 3A shows the nucleotide sequence (SEQ ID NO: 35) and amino acid sequence (SEQ ID NO: 27) of the heavy chain variable region of the 11E2 human monoclonal antibody. The CDR1 (SEQ ID NO: 3), CDR2 (SEQ ID NO: 7) and CDR3 (SEQ ID NO: 11) regions are delineated.

FIG. 3B shows the nucleotide sequence (SEQ ID NO: 39) and amino acid sequence (SEQ ID NO: 31) of the light chain variable region of the 11E2 human monoclonal antibody. The CDR1 (SEQ ID NO: 15), CDR2 (SEQ ID NO: 19) and CDR3 (SEQ ID NO: 23) regions are delineated.

FIG. 4A shows the nucleotide sequence (SEQ ID NO: 36) and amino acid sequence (SEQ ID NO: 28) of the heavy chain variable region of the 9D4 human monoclonal antibody. The CDR1 (SEQ ID NO: 4), CDR2 (SEQ ID NO: 8) and CDR3 (SEQ ID NO: 12) regions are delineated.

FIG. 4B shows the nucleotide sequence (SEQ ID NO: 40) and amino acid sequence (SEQ ID NO: 32) of the light chain variable region of the 9D4 human monoclonal antibody. The CDR1 (SEQ ID NO: 16), CDR2 (SEQ ID NO: 20) and CDR3 (SEQ ID NO: 24) regions are delineated.

FIG. 5 shows the alignment of the amino acid sequence of the heavy chain variable region of 3F11 with the human germline $V_H$ 4-34 amino acid sequence (SEQ ID NO: 41).

FIG. 6 shows the alignment of the amino acid sequence of the heavy chain variable region of 4G5 with the human germline $V_H$ 4-34 amino acid sequence (SEQ ID NO: 41).

FIG. 7 shows the alignment of the amino acid sequence of the heavy chain variable region of 11E2 and 9D4 with the human germline $V_H$ 5-51 amino acid sequence (SEQ ID NO: 42).

FIG. 8 shows the alignment of the amino acid sequence of the light chain variable region of 3F11 with the human germline $V_k$ L18 amino acid sequence (SEQ ID NO: 43).

FIG. 9 shows the alignment of the amino acid sequence of the light chain variable region of 4G5 with the human germline $V_k$ L18 amino acid sequence (SEQ ID NO: 43).

FIG. 10 shows the alignment of the amino acid sequence of the light chain variable region of 11E2 and 9D4 with the human germline $V_k$ A27 amino acid sequence (SEQ ID NO: 44).

DETAILED DESCRIPTION OF THE INVENTION

Figure 11:
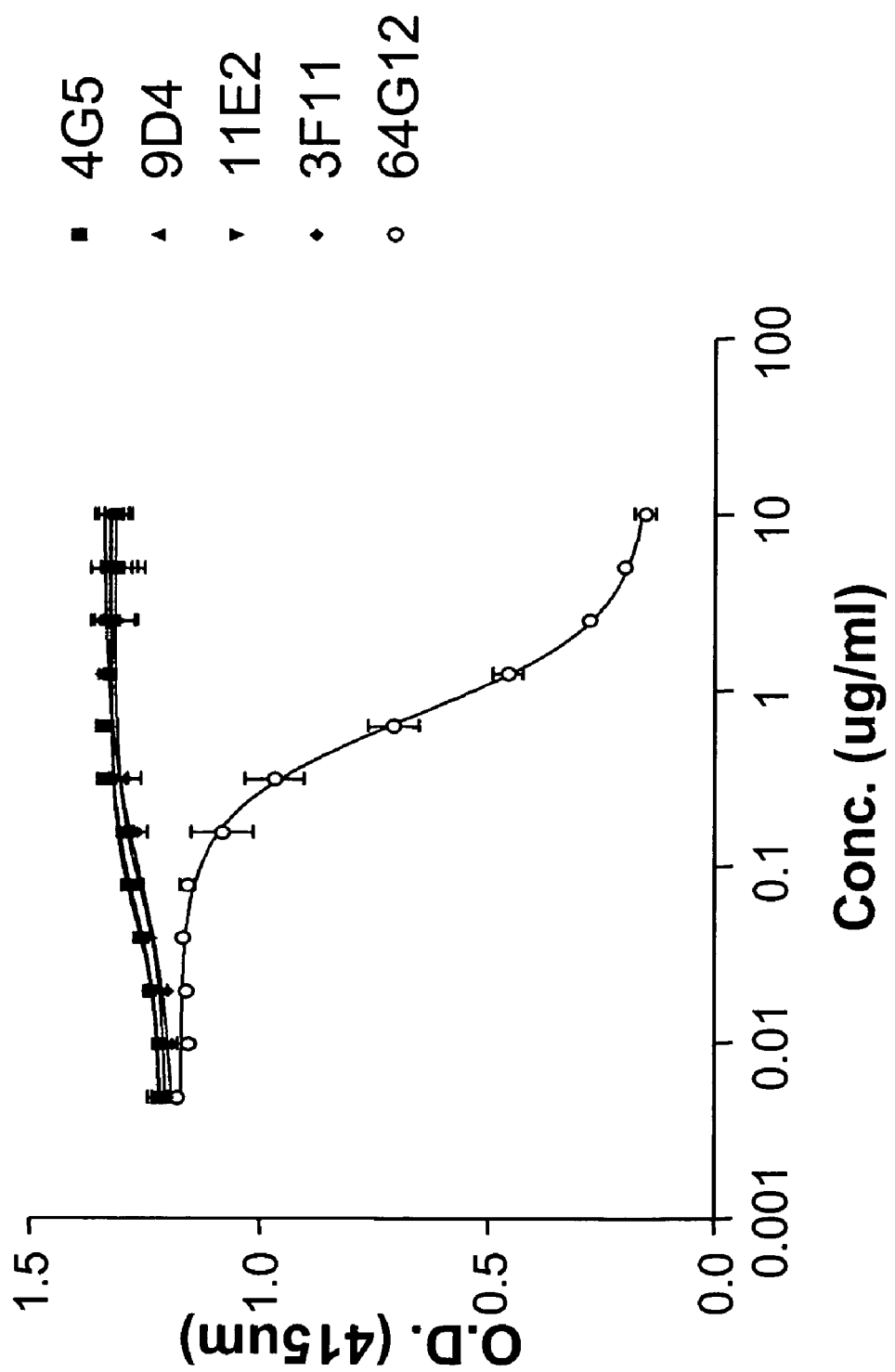
FIG. 11 is a graph showing the results of experiments demonstrating that the human monoclonal antibody, 3F11, directed against human IFNAR-1, does not compete with the mouse monoclonal antibody 64G12 for binding to IFNAR-1.

The present invention relates to isolated monoclonal antibodies that bind to Interferon alpha receptor 1 (IFNAR-1) and that are capable of blocking the action of type I interferons. The invention provides isolated antibodies, methods of making such antibodies, immunoconjugates and bispecific molecules comprising such antibodies and pharmaceutical compositions containing the antibodies, immunconjugates or bispecific molecules of the invention. The invention also relates to methods of using the antibodies to inhibit the binding of a type I interferon to IFNAR-1 on a cell expressing IFNAR-1, for example, in the treatment of immune mediated disorders, including autoimmune disorders, transplant rejection and Graft Versus Host Disease (GVHD), in a subject.

In order that the present invention may be more readily understood, certain terms are first defined. Additional definitions are set forth throughout the detailed description.

The terms "Interferon alpha receptor-1," "IFNAR-1," and "IFNAR-1 antigen" are used interchangeably, and include variants, isoforms, species homologs of human IFNAR-1, and analogs having at least one common epitope with IFNAR-1. Accordingly, human antibodies of the invention may, in certain cases, cross-react with IFNAR-1 from species other than human, or other proteins which are structurally related to human IFNAR-1 (e.g., human IFNAR-1 homologs). In other cases, the antibodies may be completely specific for human IFNAR-1 and not exhibit species or other types of cross-reactivity.

The complete cDNA sequence of human IFNAR-1 has the Genbank accession number NM_000629.

The term "type I interferon" as used herein is intended to refer to members of the type I interferon family of molecules that are ligands for IFNAR-1 (i.e., members of the type I interferon family of molecules that are capable of binding IFNAR-1). Examples of type I interferon ligands are interferon alpha 1, 2a, 2b, 4, 5, 6, 7, 8, 10, 14, 16, 17, 21, interferon beta and interferon omega.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the IFNAR-1 receptor.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., IFNAR-1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al, (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds IFNAR-1 is substantially free of antibodies that specifically bind antigens other than IFNAR-1). An isolated antibody that specifically binds IFNAR-1 may, however, have cross-reactivity to other antigens, such as IFNAR-1 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgGI) that is encoded by the heavy chain constant region genes.

As used herein, "specific binding" refers to antibody binding to a predetermined antigen. Typically, the antibody binds with a dissociation constant ($K_D$) of $10^{-7}$ M or less, and binds to the predetermined antigen with a $K_D$ that is at least two-fold less than its $K_D$ for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$ M or less and even more preferably $10^{-10}$ M or less. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

As used herein, the term "subject" includes any human or nonhuman animal. The term "nonhuman animal" includes all vertebrates, e.g., mammals and non-mammals, such as non-human primates, sheep, dogs, cats, horses, cows chickens, amphibians, reptiles, etc.

Various aspects of the invention are described in further detail in the following subsections.

Anti-IFNAR-1 Antibodies

The antibodies of the invention are characterized by particular functional features or properties of the antibodies. For example, the antibodies bind specifically to IFNAR-1, preferably human IFNAR-1. Additionally, the antibodies may cross react with IFNAR-1 from one or more non-human primates, such as cynomolgus monkey and/or rhesus monkey. Preferably, an antibody of the invention binds to IFNAR-1 with high affinity, for example with a $K_D$ of $10^{-7}$ M or less, more preferably with a $K_D$ of $10^{-8}$ M or less or $10^{-9}$ M or less or even $5 \times 10^{-10}$ M or less or $2 \times 10^{-10}$ M or less.

Furthermore, the antibodies of the invention are capable of inhibiting the biological activity of type 1 interferons. The antibodies inhibit the biological activity of at least one type I interferon, and preferably inhibit the biological activity of multiple type I interferons (i.e., at least two, more preferably at least three, or at least four, or at least five, or at least six, or at least seven, or at least eight, or at least nine, or at least ten, or at least 11, or at least 12, or at least 13 or at least 14 or at least 15, different subtypes of type I interferon). In a preferred embodiment, the antibody inhibits the biological activity of the following type I interferons: α1, α2a, α2b, α4, α5, α6, α7, α8, α10, α14, α16, α17, α21, beta and omega. In other preferred embodiments, the antibody inhibits the activity of lymphoblastoid IFN and/or leukocyte IFN.

The ability of an antibody to inhibit the biological activity of type I interferons can be examined in one or more assays established in the art. Non-limiting examples include inhibition of Type I IFN-mediated inhibition of Daudi cell proliferation, inhibition of Type I IFN-induced expression of IP-10 by peripheral blood mononuclear cells (PBMC), inhibition of dendritic cell development mediated by Systemic Lupus Erythematosus (SLE) plasma, and inhibition of the anti-viral activity of Type I IFN. At antibody "inhibits the biological activity of type I interferons" if it inhibits the activity by at least 20%, more preferably by at least 30%, even more preferably by at least 40%, at least 50%, at least 60%, at least 70%, at least 80% or at least 90%, as compared to a non-specific, control antibody.

In preferred embodiments, the antibody inhibits the activity of IFN α2b in a Daudi cell proliferation assay, inhibits the activity of IFN omega in a Daudi cell proliferation assay, inhibits IP-10 secretion by PBMC induced by IFN α2b or IFN omega, and/or inhibits dendritic cell development mediated by SLE plasma.

In another preferred embodiment, the antibody does not cross-compete with (i.e., binds to a different epitope than) the murine anti-IFNAR-1 antibody 64G12 (deposited as ECACC Deposit No. 92022605).

Assays to evaluate the functional activities of anti-IFNAR antibodies are described in further detail in the Examples. Preferred antibodies of the invention exhibit at least one, more preferably two, three, four, five or more, of the following properties:

a) specifically binds to IFNAR1 (preferably human IFNAR1);

b) binds to IFNAR1 with high affinity, such as a $K_D$ of $1 \times 10^{-8}$ M or greater affinity;

c) inhibits the biological activity of multiple Type I interferons;

d) inhibits the activity of IFN α2b in a Daudi cell proliferation assay;

e) inhibits the activity of IFN omega in a Daudi cell proliferation assay;

f) inhibits IP-10 secretion by peripheral blood mononuclear cells induced by IFN α2b;

g) inhibits IP-10 secretion by peripheral blood mononuclear cells induced by IFN omega;

h) inhibits dendritic cell development mediated by Systemic Lupus Erythematosus plasma; and i) binds to a different epitope than (i.e., does not cross-compete with) murine monoclonal antibody 64G12 (ECACC Deposit No. 92022605).

Any combination of the above-described functional features, and/or the functional features as described in the Examples, may be exhibited by an antibody of the invention.

Monoclonal Antibody 3F11, 4G5, 11E2. and 9D4

Preferred antibodies of the invention are the human monoclonal antibodies 3F11, 4G5, 11E2, and 9D4, isolated and structurally characterized as described in the Examples. The $V_H$ amino acid sequences of 3F11, 4G5, 11E2, and 9D4 are shown in SEQ ID NOs: 25, 26, 27, and 28, respectively. The $V_L$ amino acid sequences of 3F11, 4G5, 11E2, and 9D4 are shown in SEQ ID NOs: 29, 30, 31, and 32, respectively.

Given that each of these antibodies can bind to IFNAR-1, the $V_H$ and $V_L$ sequences can be "mixed and matched" to create other anti-IFNAR-1 binding molecules of the invention. IFNAR-1 binding of such "mixed and matched" antibodies can be tested using the binding assays described herein (e.g., ELISAs) and/or using the type I IFN functional inhibition assays described in the Examples. Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence. For example, the $V_H$ and $V_L$ sequences of 3F11 and 4G5 are particularly amenable for mixing and matching, since these antibodies use $V_H$ and $V_L$ sequences derived from the same germline sequences ($V_H$ 4-34 and $V_k$ L18) and thus they exhibit structural similarity. In addition, the $V_H$ and $V_L$ sequences of 11E2 and 9D4 are particularly amenable for mixing and matching, since these antibodies use $V_H$ and $V_L$ sequences derived from the same germline sequences ($V_H$ 5-51 and $V_k$ A27) and thus they exhibit structural similarity.

Accordingly, in one aspect, the invention provides an isolated monoclonal antibody, or antigen binding portion thereof, comprising:

(a) a heavy chain variable region comprising an amino acid sequence selected from the group consisting of SEQ ID NOs: 25, 26, 27, and 28; and (b) a light chain variable region comprising an amino acid sequence selected from the group consisting of SEQ ID NOs: 29, 30, 31, and 32;

wherein the antibody specifically binds IFNAR-1.

Preferred heavy and light chain combinations include:

(a) a heavy chain variable region comprising the amino acid sequence of SEQ ID NO: 25; and (b) a light chain variable region comprising the amino acid sequence of SEQ ID NO: 29; or (a) a heavy chain variable region comprising the amino acid sequence of SEQ ID NO: 26; and (b) a light chain variable region comprising the amino acid sequence of SEQ ID NO: 30; or (a) a heavy chain variable region comprising the amino acid sequence of SEQ ID NO: 27; and (b) a light chain variable region comprising the amino acid sequence of SEQ ID NO: 31; or (a) a heavy chain variable region comprising the amino acid sequence of SEQ ID NO: 28; and (b) a light chain variable region comprising the amino acid sequence of SEQ ID NO: 32.

In another aspect, the invention provides antibodies that comprise the heavy chain and light chain CDR1s, CDR2s and CDR3s of 3F11, 4G5, 11E2, and 9D4, or combinations thereof. The amino acid sequences of the $V_H$ CDR1s of 3F11, 4G5, 11E2, and 9D4 are shown in SEQ ID NOs: 1, 2, 3, and 4. The amino acid sequences of the $V_H$ CDR2s of 3F11, 4G5, 11E2, and 9D4 are shown in SEQ ID NOs: 5, 6, 7, and 8. The amino acid sequences of the $V_H$ CDR3s of 3F11, 4G5, 11E2, and 9D4 are shown in SEQ ID NOs: 9, 10, 11, and 12. The amino acid sequences of the $V_k$ CDR1s of 3F11, 4G5, 11E2, and 9D4 are shown in SEQ ID NOs: 13, 14, 15, and 16. The amino acid sequences of the $V_k$ CDR2s of 3F11, 4G5, 11E2, and 9D4 are shown in SEQ ID NOs: 17, 18, 19, and 20. The amino acid sequences of the $V_k$ CDR3s of 3F11, 4G5, 11E2, and 9D4 are shown in SEQ ID NOs: 21, 22, 23, and 24. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to IFNAR-1 and that antigen-binding specificity is provided primarily by the CDR1, 2 and 3 regions, the $V_H$ CDR1, 2 and 3 sequences and $V_k$ CDR1, 2 and 3 sequences can be "mixed and matched" (i.e., CDRs from different antibodies can be mixed and match, although each antibody must contain a $V_H$ CDR1, 2 and 3 and a $V_k$ CDR1, 2 and 3) to create other anti-IFNAR-1 binding molecules of the invention. IFNAR-1 binding of such "mixed and matched" antibodies can be tested using the binding assays described above and in the Examples (e.g., ELISAs). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). For example, the $V_H$ CDR1s of 3F11 and 4G5 share some structural similarity and therefore are amenable to mixing and matching. As another example, the $V_H$ CDR1s of 11E2 and 9D4 share some structural similarity and therefore are amenable to mixing and matching. As yet another example, the $V_k$ CDR1s of 3F11 and 4G5 share some structural similarity. As yet another example, the $V_H$ CDR1s of 11E2 and 9D4 share some structural similarity. It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies antibodies 3F11, 4G5, 11E2, and 9D4.

Accordingly, in another aspect, the invention provides an isolated monoclonal antibody, or antigen binding portion thereof comprising:

(a) a heavy chain variable region CDR1 comprising an amino acid sequence selected from the group consisting of SEQ ID NOs: 1, 2, 3, and 4;

(b) a heavy chain variable region CDR2 comprising an amino acid sequence selected from the group consisting of SEQ ID NOs: 5, 6, 7, and 8;

(c) a heavy chain variable region CDR3 comprising an amino acid sequence selected from the group consisting of SEQ ID NOs: 9, 10, 11, and 12;

(d) a light chain variable region CDR1 comprising an amino acid sequence selected from the group consisting of SEQ ID NOs: 13, 14, 15, and 16;

(e) a light chain variable region CDR2 comprising an amino acid sequence selected from the group consisting of SEQ ID NOs: 17, 18, 19, and 20; and (f) a light chain variable region CDR3 comprising an amino acid sequence selected from the group consisting of SEQ ID NOs: 21, 22, 23, and 24;

wherein the antibody specifically binds IFNAR-1.

In a preferred embodiment, the antibody comprises:

(a) a heavy chain variable region CDR1 comprising SEQ ID NO: 1;

(b) a heavy chain variable region CDR2 comprising SEQ ID NO: 5;

(c) a heavy chain variable region CDR3 comprising SEQ ID NO: 9;

(d) a light chain variable region CDR1 comprising SEQ ID NO: 13;

(e) a light chain variable region CDR2 comprising SEQ ID NO: 17; and (f) a light chain variable region CDR3 comprising SEQ ID NO: 21.

In another preferred embodiment, the antibody comprises:

(a) a heavy chain variable region CDR1 comprising SEQ ID NO: 2;

(b) a heavy chain variable region CDR2 comprising SEQ ID NO: 6;

(c) a heavy chain variable region CDR3 comprising SEQ ID NO: 10;

(d) a light chain variable region CDR1 comprising SEQ ID NO: 14;

(e) a light chain variable region CDR2 comprising SEQ ID NO: 18; and (f) a light chain variable region CDR3 comprising SEQ ID NO: 22.

In another preferred embodiment, the antibody comprises:
  (a) a heavy chain variable region CDR1 comprising SEQ ID NO: 3;
  (b) a heavy chain variable region CDR2 comprising SEQ ID NO: 7;
  (c) a heavy chain variable region CDR3 comprising SEQ ID NO: 11;
  (d) a light chain variable region CDR1 comprising SEQ ID NO: 15;
  (e) a light chain variable region CDR2 comprising SEQ ID NO: 19; and
  (f) a light chain variable region CDR3 comprising SEQ ID NO: 23.

In another preferred embodiment, the antibody comprises:
  (a) a heavy chain variable region CDR1 comprising SEQ ID NO: 4;
  (b) a heavy chain variable region CDR2 comprising SEQ ID NO: 8;
  (c) a heavy chain variable region CDR3 comprising SEQ ID NO: 12;
  (d) a light chain variable region CDR1 comprising SEQ ID NO: 16;
  (e) a light chain variable region CDR2 comprising SEQ ID NO: 20; and
  (f) a light chain variable region CDR3 comprising SEQ ID NO: 24.

Antibodies that Bind to the Same Epitope as 3F11, 4G5, 11E2, and 9D4

In another embodiment, the invention provides antibodies that bind to the same epitope on human IFNAR-1 as the monoclonal antibodies 3F11, 4G5, 11E2, or 9D4 (having $V_H$ sequences as shown in SEQ ID NOs: 25, 26, 27, and 28, respectively, and $V_L$ sequences as shown in SEQ ID NOs: 29, 30, 31, 32, respectively). Such antibodies can be identified based on their ability to cross-compete with 3F11, 4G5, 11E2, or 9D4 in standard IFNAR-1 binding assays. The ability of a test antibody to inhibit the binding of 3F11, 4G5, 11E2, or 9D4 to human IFNAR-1 demonstrates that the test antibody can compete with 3F11, 4G5, 11E2, or 9D4 for binding to human IFNAR-1 and thus binds to the same epitope on human IFNAR-1 as 3F11, 4G5, 11E2, or 9D4. In a preferred embodiment, the antibody that binds to the same epitope on human IFNAR-1 as 3F11, 4G5, 11E2, or 9D4 is a human monoclonal antibody. Such human monoclonal antibodies can be prepared and isolated as described in the Examples.

In another preferred embodiment, the antibody binds to a different epitope than (i.e., does not cross-compete with) the mouse monoclonal antibody 64G12 (ECACC Deposit No. 92022605).

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, the invention provides an isolated anti-IFNAR-1 monoclonal antibody, or an antigen-binding portion thereof, wherein the antibody:
  (a) comprises a heavy chain variable region of a human $V_H$ 4-34 or 5-51 gene;
  (b) comprises a light chain variable region of a human $V_k$ L18 or A27 gene; and
  (c) the antibody specifically binds to IFNAR-1.

Examples of antibodies having $V_H$ and $V_k$ of $V_H$ 4-34 and Vk L18, respectively, include 3F11 and 4G5. Examples of antibodies having $V_H$ and $V_k$ of VH 5-51 and Vk A27, respectively, include 11E2 and 9D4.

As used herein, a human antibody comprises heavy or light chain variable regions "of" or "derived from" or "the product of" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "of" or "derived from" or "the product of" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "of" or "derived from" or "the product of" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-IFNAR-1 antibodies of the invention. For example, the invention provides an isolated monoclonal antibody, or antigen binding portion thereof, comprising a heavy chain variable region and a light chain variable region, wherein:
  (a) the heavy chain variable region comprises an amino acid sequence That is at least 80% homologous to an amino acid sequence selected from the group consisting of SEQ ID NOs: 25, 26, 27, and 28;
  (b) the light chain variable region comprises an amino acid sequence that is at least 80% homologous to an amino acid sequence selected from the group consisting of SEQ ID NOs: 29, 30, 31, and 32;
  (c) the antibody specifically binds to IFNAR-1 and exhibits at least one of the functional properties described herein, preferably several of the functional properties described herein.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs: 33, 34, 35, 36, 37, 38, 39, or 40, followed by testing of the encoded altered antibody for retained function (i.e., the functions set forth in (c), (d) and (e) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total# of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17(1998)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 3F11, 4G5, 11E2, and 9D4), or conservative modifications thereof, and wherein the antibodies retain the desired functional properties of the anti-IFNAR-1 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 9, 10, 11, and 12, and conservative modifications thereof;
(b) the light chain variable region CDR3 sequence comprises an amino acid sequence selected from the group consisting of amino acid sequences of SEQ ID NOs: 21, 22, 23, and 24, and conservative modifications thereof; and
(c) the antibody specifically binds to IFNAR-1 and exhibits at least one of the functional properties described herein, more preferably several of the functional properties described herein.

In a further embodiment, the heavy chain variable region CDR2 sequence comprises an amino acid sequence selected from the group consisting of amino acid sequences of SEQ ID NOs: 5, 6, 7, and 8, and conservative modifications thereof; and the light chain variable region CDR2 sequence comprises an amino acid sequence selected from the group consisting of amino acid sequences of SEQ ID NOs: 17, 18, 19, and 20, and conservative modifications thereof. In a still further embodiment, the heavy chain variable region CDR1 sequence comprises an amino acid sequence selected from the group consisting of amino acid sequences of SEQ ID NOs: 1, 2, 3, and 4, and conservative modifications thereof; and the light chain variable region CDR1 sequence comprises an amino acid sequence selected from the group consisting of amino acid sequences of SEQ ID NOs: 13, 14, 15, and 16, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c), (d) and (e) above) using the functional assays described herein.

Engineered and Modified Antibodies

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising: a heavy chain variable region comprising CDR1, CDR2, and CDR3 sequences comprising an amino acid sequence selected from the group consisting of SEQ ID NOs: 1, 2, 3, and 4, SEQ ID NOs: 5, 6, 7, and 8 and SEQ ID NOs: 9, 10, 11, and 12, respectively, and a light chain variable region comprising CDR1, CDR2, and CDR3 sequences comprising an amino acid sequence selected from the group consisting of SEQ ID NOs: 13, 14, 15, and 16, SEQ ID NOs: 17, 18, 19, and 20 and SEQ ID NOs: 21, 22, 23, and 24, respectively. Thus, such antibodies contain the $V_H$ and $V_L$ CDR sequences of monoclonal antibodies 3F11, 4G5, 11E2, or 9D4 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies of the invention are those that are structurally similar to the framework sequences used by selected antibodies of the invention, e.g., similar to the $V_H$ 4-34 and $V_L$ L18 framework sequences used by the 3F11 and 4G5 monoclonal antibodies, or the $V_H$ 5-51 and $V_L$ A27 framework sequences used by the 11E2 and 9D4 monoclonal antibodies. The $V_H$ CDR1, 2 and 3 sequences of SEQ ID NOs: 1, 2, 3, 4, 5, 6, 7, 8, 9, 10, 11 and 12, and the $V_L$ CDR1, 2 and 3 sequences of SEQ ID NOs: 13, 14, 15, 16, 17, 18, 19, 20, 21, 22, 23, and 24 can be grafted onto framework regions that have the same sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than five residues are altered within a CDR region are altered.

Accordingly, in another embodiment, the invention provides isolated anti-IFNAR-1 monoclonal antibodies, or antigen binding portions thereof, comprising a heavy chain variable region comprising: (a) a $V_H$ CDR1 region comprising an amino acid sequence selected from the group consisting of SEQ ID NO: 1, 2, 3, and 4, or an amino acid sequence having one, two, three, four or five amino acid substitutions, deletions or additions as compared to an amino acid sequence selected from the group consisting of SEQ ID NO: 1, 2, 3, and 4; (b) a $V_H$ CDR2 region comprising an amino acid sequence selected from the group consisting of SEQ ID NO: 5, 6, 7, and 8, or an amino acid sequence having one, two, three, four or five amino acid substitutions, deletions or additions as compared to an amino acid sequence selected from the group consisting of SEQ ID NO: 5, 6, 7, and 8; (c) a $V_H$ CDR3 region comprising an amino acid sequence selected from the group consisting of SEQ ID NO: 9, 10, 11, and 12, or an amino acid sequence having one, two, three, four or five amino acid substitutions, deletions or additions as compared to an amino acid sequence selected from the group consisting of SEQ ID NO: 9, 10, 11, and 12; (d) a $V_L$ CDR1 region comprising an amino acid sequence selected from the group consisting of SEQ ID NO: 13, 14, 15, and 16, or an amino acid sequence having one, two, three, four or five amino acid substitutions, deletions or additions as compared to an amino acid sequence selected from the group consisting of SEQ ID NO: 13, 14, 15, and 16; (e) a $V_L$ CDR2 region comprising an amino acid sequence selected from the group consisting of SEQ ID NO: 17, 18, 19, and 20, or an amino acid sequence having one, two, three, four or five amino acid substitutions, deletions or additions as compared to an amino acid sequence selected from the group consisting of SEQ ID NO: 17, 18, 19, and 20; and (f) a $V_L$ CDR3 region comprising an amino acid sequence selected from the group consisting of SEQ ID NO: 21, 22, 23, and 24, or an amino acid sequence having one, two, three, four or five amino acid substitutions, deletions or additions as compared to an amino acid sequence selected from the group consisting of SEQ ID NO: 17, 18, 19, and 20.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. For example, for 3F11, amino acid residue #43 (within FR2) of $V_H$ is a threonine whereas this residue in the corresponding $V_H$ 4-34 germline sequence is an alanine (see FIG. 5). To return the framework region sequences to their germline configuration, the somatic mutations can be "backmutated" to the germline sequence by, for example, site-directed mutagenesis or PCR-mediated mutagenesis (e.g., residue 43 of the $V_H$ of 3F11 can be "backmutated" from threonine to alanine). As another example, for 4G5, amino acid residue #81 (within FR3) of $V_H$ is an asparagine whereas this residue in the corresponding $V_H$ 4-34 germline sequence is a lysine (see FIG. 6). To return the framework region sequences to their germline configuration, the somatic mutations can be "backmutated" to from asparagine to lysine. As another example, for 11E2 and 9D4, amino acid residue #28 (within FR1) of $V_H$ is an isoleucine whereas this residue in the corresponding $V_H$ 5-51 germline sequence is a serine (see FIG. 7). To return the framework region sequences to their germline configuration, the somatic mutations can be "backmutated" to from isoleucine to serine. Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter it's glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) J. Biol. Chem. 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

Thus, in another aspect of the invention, the structural features of anti-IFNAR-1 antibodies of the invention, e.g. 3F11, 4G5, 11E2, and 9D4 are used to create structurally related anti-IFNAR-1 antibodies that retain at least one functional property of the antibodies of the invention, such as binding to IFNAR-1. For example, one or more CDR regions of 3F11, 4G5, 11E2, or 9D4, or mutations thereof, can be combined recombinantly with known framework regions and/or other CDRs to create additional, recombinantly-engineered, anti-IFNAR-1 antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-IFNAR-1 antibody comprising:
(a) providing: (i) a heavy chain variable region antibody sequence comprising a CDR1 sequence selected from the group consisting of SEQ ID NOs: 1, 2, 3 and 4, a CDR2 sequence selected from the group consisting of SEQ ID NOs: 5, 6, 7, and 8 and/or a CDR3 sequence selected from the group consisting of SEQ ID NOs: 9, 10, 11, and 12; and (ii) a light chain variable region antibody sequence comprising a CDR1 sequence selected from the group consisting of SEQ ID NOs: 13, 14, 15, and 16, a CDR2 sequence selected from the group consisting of SEQ ID NOs: 17, 18, 19, and 20 and/or a CDR3 sequence selected from the group consisting of SEQ ID NOs: 21, 22, 23, and 24;
(b) altering at least one amino acid residue within the first antibody sequence and/or the second antibody sequence to create at least one altered antibody sequence; and
(c) preparing the altered antibody sequence; and
(d) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-IFNAR-1 antibodies described herein, which functional properties include, but are not limited to:
(i) binding to IFNAR-1;
(ii) inhibiting the binding of type I interferons to IFNAR-1;
(iii) binding to live cells expressing human IFNAR-1;
(iv) binding to human IFNAR-1 with a $K_D$ of $10^{-8}$ M or less (e.g., $10^{-9}$ M or $10^{-10}$ M or less);
(v) binding to a unique epitope on IFNAR-1 (to eliminate the possibility that monoclonal antibodies with complimentary activities when used in combination would compete for binding to the same epitope).

The functional properties of the altered antibodies can be assessed using standard assays available in the art and/or described herein. For example, the ability of the antibody to bind IFNAR-1 can be determined using standard binding assays, such as those set forth in the Examples (e.g., ELISAs).

In certain embodiments of the methods of engineering antibodies of the invention, mutations can be introduced randomly or selectively along all or part of an anti-IFNAR-1 antibody coding sequence (e.g., 3F11, 4G5, 11E2, or 9D4 coding sequence) and the resulting modified anti-IFNAR-1 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the VH and VL sequences of the 3F11, 4G5, 11E2, and 9D4 monoclonal antibodies. DNA sequences encoding the 3F11 VH and VL sequences are shown in SEQ ID NOs: 33 and 37, respectively. DNA sequences encoding the 4G5 VH and VL sequences are shown in SEQ ID NOs: 34 and 38, respectively. DNA sequences encoding the 11E2 VH and VL sequences are shown in SEQ ID NOs: 35 and 39, respectively. DNA sequences encoding the 9D4 VH and VL sequences are shown in SEQ ID NOs: 36 and 40, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against IFNAR-1 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HUMAB MOUSE® (MEDAREX, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ. monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of HuMab mice, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Nati. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-85 1, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-IFNAR-1 antibodies of the invention. For example, an alternative transgenic system referred to as the XENOMOUSE (ABGENIX, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-IFNAR-1 antibodies of the invention. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-IFNAR-1 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of IFNAR-1 antigen and/or cells expressing IFNAR-1, as described by Lonberg, N. et al. (1994) Nature 368(6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or enriched preparation (5-50 µg) of IFNAR-1 antigen can be used to immunize the human Ig mice intraperitoneally. In the event that immunizations using a purified or enriched preparation of IFNAR-1 antigen do not result in antibodies, mice can also be immunized with cells expressing IFNAR-1, e.g., a human T-cell line, to promote immune responses.

Detailed procedures to generate fully human monoclonal antibodies to IFNAR-1 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-IFNAR-1 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12).

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1 X HAT (SIGMA; the HAT is added 24 hours after the fusion). After approximately two weeks, cells can be cultured in medium in which the HAT is replaced with HT. Individual wells can then be screened by ELISA for human monoclonal 1gM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to IFNAR-1 by, for example, standard ELISA. Briefly, microtiter plates are coated with purified IFNAR-1 at 0.25 µg/ml in PBS, and then blocked with 5% bovine serum albumin in PBS. Dilutions of antibody (e.g., dilutions of plasma from IFNAR-1-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with IFNAR-1 immunogen. Hybridomas that bind with high avidity to IFNAR-1 are subcloned and further characterized. One clone from each hybridoma, which retains the reactivity of the parent cells (by ELISA), can be chosen for making a 5-10 vial cell bank stored at −140° C., and for antibody purification.

To purify anti-IFNAR-1 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-IFNAR-1 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using IFNAR-1 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To demonstrate binding of monoclonal antibodies to live cells expressing IFNAR-1, flow cytometry can be used. Briefly, cell lines expressing IFNAR-1 (grown under standard growth conditions) are mixed with various concentrations of monoclonal antibodies in PBS containing 0.1% BSA and 10% fetal calf serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-IFNAR-1 human IgGs can be further tested for reactivity with IFNAR-1 antigen by Western blotting. Briefly, cell extracts from cells expressing IFNAR-1 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (SIGMA Chem. Co., St. Louis, Mo.)

Immunoconjugates

In another aspect, the present invention features an anti-IFNAR-1 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins". A cytotoxin or cytotoxic agent includes any agent that is detrimental to (e.g., kills) cells. Examples include TAXOL, cytochalasin B, gramicidin D, ethidium bromide, emetine, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinbiastine).

Other preferred examples of therapeutic cytotoxins that can be conjugated to an antibody of the invention include duocarmycins, calicheamicins, maytansines and auristatins, and derivatives thereof An example of a calicheamicin antibody conjugate is commercially available (MYLOTARG™; WYETH-AYERST).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-I"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-IFNAR-1 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for IFNAR-1 and a second binding specificity for a second target epitope. In a particular embodiment of the invention, the second target epitope is an Fc receptor, e.g., human FcγRI (CD64) or a human Fcα receptor (CD89). Therefore, the invention includes bispecific molecules capable of binding both to FcγR, FcαR or FcεR expressing effector cells (e.g., monocytes, macrophages or polymorphonuclear cells (PMNs)), and to target cells expressing IFNAR-1. These bispecific molecules target IFNAR-1 expressing cells to effector cell and trigger Fc receptor-mediated effector cell activities, such as phagocytosis of an IFNAR-1 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-IFNAR-1 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_C$ receptor or target cell antigen. The "anti-enhancement factor portion" can bind an $F_C$ receptor or a target cell antigen.

Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγreceptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of certain preferred anti-Fcγmonoclonal antibodies are described by Fanger et al. in PCT Publication WO 88/00052 and in U.S. Pat. No. 4,954, 617, the teachings of which are fully incorporated by reference herein. These antibodies bind to an epitope of FcγRI, FcγRII or FcγRIII at a site which is distinct from the Fcγbinding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγreceptor antibody is a humanized form of monoclonal antibody 22 (H22). The production and characterization of the H22 antibody is described in Graziano, R. F. et al. (1995) *J. Immunol* 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7 \, M^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-IFNAR-1 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) *Behring Ins. Mitt. No.* 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013, 653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a y counter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-IFNAR-1 antibody of the present invention combined with at least one other immunosuppressing agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred per cent, this amount will range from about 0.01 per cent to about ninety-nine percent of active ingredient, preferably from about 0.1 per cent to about 70 per cent, most preferably from about 1 per cent to about 30 per cent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-IFNAR-1 antibody of the invention include 1 mg/kg body weight or 3 mg/kg body weight via intravenous administration, with the antibody being given using one of the following dosing schedules: (i) every four weeks for six dosages, then every three months; (ii)

every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-IFNAR-1 antibody of the invention preferably results in a decrease in severity of disease symptoms, an increase in frequency and duration of disease symptom-free periods, or a prevention of impairment or disability due to the disease affliction. In the case of, for example, Systemic Lupus Erythematosus (SLE), a therapeutically effective dose preferably prevents further deterioration of physical symptoms associated with SLE, such as, for example, pain, fatigue or weakness. A therapeutically effective dose preferably also prevents or delays onset of SLE, such as may be desired when early or preliminary signs of the disease are present. Likewise it includes delaying chronic progression associated with SLE. Laboratory tests utilized in the diagnosis of SLE include chemistries, hematology, serology and radiology. Accordingly, any clinical or biochemical assay that monitors any of the foregoing may be used to determine whether a particular treatment is a therapeutically effective dose for treating SLE. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Invention

The antibodies (and immunoconjugates and bispecific molecules) of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders. The term "subject" as used herein in intended to includes human and non-human animals. Non-human animals includes all vertebrates, e.g., mammals and non-mammals, such as non-human primates, sheep, dogs, cats, cows, horses, chickens, amphibians, and reptiles. The methods are particularly suitable for treating human patients having a disorder associated with aberrant or inappropriate Type I interferon expression (e.g., overexpression).

When antibodies to IFNAR-1 are administered together with another agent, the two can be administered in either order or simultaneously. For example, an anti-IFNAR-1 antibody of the invention can be used in combination with one or more of the following agents: anti-IFNα antibody, anti-IFNγ receptor antibody, soluble IFNγ receptor, anti-TNF antibody, anti-TNF receptor antibody and/or soluble TNF receptor (see e.g., U.S. Pat. No. 5,888,511). Furthermore, an anti-IFNAR-1 antibody of invention can be used in combination with a Flt3 ligand antagonist (see e.g., U.S. application No. 2002/0160974).

In one embodiment, the antibodies (and immunoconjugates and bispecific molecules) of the invention can be used to detect levels of IFNAR-1, or levels of cells that express IFNAR-1. This can be achieved, for example, by contacting a sample (such as an in vitro sample) and a control sample with the anti-IFNAR-1 antibody under conditions that allow for the formation of a complex between the antibody and IFNAR-1. Any complexes formed between the antibody and IFNAR-1 are detected and compared in the sample and the control. For example, standard detection methods, well-known in the art, such as ELISA and flow cytometic assays, can be performed using the compositions of the invention.

Accordingly, in one aspect, the invention further provides methods for detecting the presence of IFNAR-1 (e.g., human IFNAR-1 antigen) in a sample, or measuring the amount of IFNAR-1, comprising contacting the sample, and a control sample, with an antibody of the invention, or an antigen binding portion thereof, which specifically binds to IFNAR-1, under conditions that allow for formation of a complex between the antibody or portion thereof and IFNAR-1. The formation of a complex is then detected, wherein a difference in complex formation between the sample compared to the control sample is indicative of the presence of IFNAR-1 in the sample.

Also within the scope of the invention are kits comprising the compositions (e.g., antibodies, human antibodies, immunoconjugates and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit.

IFNAR-1 is part of the cellular receptor for Type I interferons, and Type I interferons are known to be immunoregulatory cytokines that are involved in, inter alia, T cell differentiation, antibody production and activity and survival of memory T cells. Moreover, increased expression of Type I interferons has been described in numerous autoimmune diseases, in HIV infection, in transplant rejection and in graft versus host disease (GVHD). Accordingly, the anti-IFNAR-1 antibodies (and immunoconjugates and bispecific molecules) of the invention, which inhibit the functional activity of Type I interferons, can be used in a variety of clinical indications involving aberrant or undesired Type I interferon activity. The invention, therefore, provides a method of inhibiting a Type I interferon-mediated disease or disorder, wherein the method comprises administering an antibody, or antigen-binding portion thereof, of the invention (or immunconjugate or bispecific molecule of the invention) such that the Type I interferon-mediated disease or disorder is treated.

Specific examples of autoimmune conditions in which the antibodies of the invention can be used include, but are not limited to, the following: systemic lupus erythematosus (SLE), insulin dependent diabetes mellitus (IDDM), inflammatory bowel disease (IBD) (including Crohn's Disease, Ulcerative Colitis and Celiac's Disease), multiple sclerosis (MS), psoriasis, autoimmune thyroiditis, rheumatoid arthritis (RA) and glomerulonephritis. Furthermore, the antibody compositions of the invention can be used for inhibiting or preventing transplant rejection or in the treatment of graft versus host disease (GVHD) or in the treatment of HIV infection/AIDS.

High levels of IFNα have been observed in the serum of patients with systemic lupus erythematosus (SLE) (see e.g., Kim et al. (1987) *Clin. Exp. Immunol.* 70:562-569). Moreover, administration of IFNα, for example in the treatment of cancer or viral infections, has been shown to induce SLE (Garcia-Porrua et al. (1998) *Clin. Exp. Rheumatol.* 16:107-108). Accordingly, in another embodiment, the anti-IFNAR-1 antibodies of the invention can be used in the treatment of SLE by administering the antibody to a subject in need of treatment. The antibody can be used alone or in combination with other anti-SLE agents, such as non-steroidal anti-inflammatory drugs (NSAIDs), analgesics, corticosteroids (e.g., predinisone, hydrocortisone), immunosuppressants (such as cyclophosphamide, azathioprine, and methotrexate), antimalarials (such as hydroxychloroquine) and biologic drugs that inhibit the production of dsDNA antibodies (e.g., LJP 394).

IFNα also has been implicated in the pathology of Type I diabetes. For example, the presence of immunoreactive IFNα in pancreatic beta cells of Type I diabetes patients has been reported (Foulis et al. (1987) *Lancet* 2:1423-1427). Prolonged use of IFNα in anti-viral therapy also has been shown to induce Type I diabetes (Waguri et al. (1994) *Diabetes Res. Clin. Pract.* 23:33-36). Accordingly, in another embodiment, the anti-IFNAR-1 antibodies of the invention can be used in the treatment of Type I diabetes by administering the antibody to a subject in need of treatment. The antibody can be used alone or in combination with other anti-diabetic agents, such as insulin.

Antibodies to IFNAR have been shown to be effective in an animal model of inflammatory bowel disease (see U.S. Patent Application 60/465,155). Thus, the anti-IFNAR-1 antibodies of the invention can be used in the treatment of inflammatory bowel disease (IBD), including ulcerative colitis and Crohn's disease, by administering the antibody to a subject in need of treatment. The antibody can be used alone or in combination with other anti-IBD agents, such as drugs containing mesalamine (including sulfasalazine and other agents containing 5-aminosalicylic acid (5-ASA), such as olsalazine and balsalazide), non-steroidal anti-inflammatory drugs (NSAIDs), analgesics, corticosteroids (e.g., predinisone, hydrocortisone), TNF-inhibitors (including adilimumab (HUMIRA®), etanercept (ENBREL®) and infliximab (REMICADE®)), immunosuppressants (such as 6-mercaptopurine, azathioprine and cyclosporine A), and antibiotics.

Treatment with IFNα has also been observed to induce autoimmune thyroiditis (Monzani et al. (2004) *Clin. Exp. Med.* 3:199-210; Prummel and Laurberg (2003) *Thyroid* 13:547-551). Accordingly, in another embodiment, the anti-IFNAR antibodies of the invention can be used in the treatment of autoimmune thyroid disease, including autoimmune primary hypothyroidism, Graves' Disease, Hashimoto's thyroiditis and destructive thyroiditis with hypothyroidism, by administering the antibody to a subject in need of treatment. The antibody can be used alone or in combination with other agents or treatments, such as anti-thyroid drugs, radioactive iodine and subtotal thyroidectomy.

Increased levels of type I interferons, especially IFB-β, have been observed in the serum of patients with RA (see e.g., Hertzog et al. (1988) Clin. Immunol. Immunopath. 48:192). Thus, in an embodiment, the anti-IFNAR-1 antibodies of the present invention can be used in the treatment of RA by administering the antibody to a subject in need of such treatment. The antibody can be used alone or in combination with one or more other anti-RA agent, such as a non-steroidal anti-inflammatory drug (NSAID), a COX-2 inhibitor, an analgesic, a corticosteroid (e.g., predinisone, hydrocortisone), gold, an immunosuppressant (e.g., methotrexate), a B-cell depletion agent (e.g., RITUXAN™), a B-cell agonist (e.g., LymphoStat-B™ LYMPHOSTAT-B™) and an anti-TNFα agent (e.g., EMBREL™, HUMIRA® and REMICADE™).

Administration of IFNα. has been reported to exacerbate psoriasis. Accordingly, in another embodiment, the anti-IFNAR-1 antibodies of the invention can be used in the treatment of psoriasis and psoriatic arthritis by administering the antibody to a subject in need of such treatment. The antibody can be used alone or in combination with one or more other anti-psoriasis treatments such as phototherapy, topical therapy (e.g., topical glucocorticoids), or systemic therapy (e.g., methotrexate, a synthetic retinoid, cyclosporine), an anti-TNF-α. agent (e.g., EMBREL™, HUMIRA® and REMICADE™), and a T-cell inhibitor (e.g., RAPTIVA™).

High levels of IFNα also have been observed in the circulation of patients with HIV infection and its presence is a predictive marker of AIDS progression (DeStefano et al. (1982) *J. Infec. Disease* 146:451; Vadhan-Raj et al. (1986) *Cancer Res.* 46:417). Thus, in another embodiment, an anti-IFNAR-1 antibody of the invention is used in the treatment of HIV infection or AIDS by administering the antibody to a subject in need of treatment. The antibody can be used alone or in combination with other anti-HIV agents, such as nucleoside reverse transcriptase inhibitors, non-nucleoside reverse transcriptase inhibitors, protease inhibitors and fusion inhibitors.

Antibodies to IFNAR-1 have been demonstrated to be effective in inhibiting allograft rejection and prolonging allograft survival (see e.g., Tovey et al. (1996) *J. Leukoc. Biol.* 59:512-517; Benizri et al. (1998) *J. Interferon Cytokine Res.* 18:273-284). Accordingly, the anti-IFNAR-1 antibodies of the invention also can be used in transplant recipients to inhibit allograft rejection and/or prolong allograft survival. The invention provides a method of inhibiting transplant rejection by administering an anti-IFNAR-1 antibody of the invention to a transplant recipient in need of treatment. Examples of tissue transplants that can be treated include, but are not limited to, liver, lung, kidney, heart, small bowel, and pancreatic islet cells, as well as the treatment of graft versus host disease (GVHD). The antibody can be used alone or in combination with other agents for inhibiting transplant rejection, such as immunosuppressive agents (e.g., cyclosporine, azathioprine, methylprednisolone, prednisolone, prednisone, mycophenolate mofetil, sirilimus, rapamycin, tacrolimus), anti-infective agents (e.g., acyclovir, clotrimazole, ganciclovir, nystatin, trimethoprimsulfamethoxazole), diuretics (e.g., bumetanide, furosemide, metolazone) and ulcer medications (e.g., cimetidine, famotidine, lansoprazole, omeprazole, ranitidine, sucralfate).

The present invention is further illustrated by the following examples which should not be construed as further limiting. The contents of all figures and all references, patents and published patent applications cited throughout this application are expressly incorporated herein by reference.

EXAMPLE 1

Generation of Human Monoclonal Antibodies Against IFNAR-1

Antigen

Soluble IFNAR-1, containing the extracellular domain of IFNAR-1 was generated by recombinant methods and used as antigen for immunization.

Transgenic HuMab Mice

Fully human monoclonal antibodies to IFNAR-1 were prepared using HCo7, HCo12, and HCo7xHCo12 strains of HuMab transgenic mice, each of which express human antibody genes. In each of these mouse strains, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Each of these mouse strains carries a human kappa light chain transgene, KCo5, as described in Fishwild et al. (1996) *Nature Biotechnology* 14:845-851. The HCo7 strain carries the HCo7 human heavy chain transgene as described in U.S. Pat. Nos. 5,545,806; 5,625,825; and 5,545,807. The HCo12 strain carries the HCo12 human heavy chain transgene as described in Example 2 of PCT Publication WO 01/09187. The HCo7xHCo12 stain carries both the HCo7 and the HCo12 transgenes and was made by breeding the two strains together.

HuMab Mice Immunizations:

To generate fully human monoclonal antibodies to IFNAR-1, HuMab mice were immunized with purified recombinant IFNAR-1 as antigen. General immunization schemes for HuMab mice are described in Lonberg, N. et al (1994) *Nature* 368(6474): 856-859; Fishwild, D. et al. (1996) *Nature Biotechnology* 14: 845-851 and PCT Publication WO 98/24884. The mice were 6-16 weeks of age upon the first infusion of antigen. A purified recombinant preparation (5-50 µg) of soluble IFNAR-1 antigen was used to immunize the HuMab mice intraperitonealy, subcutaneously (Sc) or via footpad injection.

Transgenic mice were immunized twice with antigen in complete Freund's adjuvatnt or Ribi adjuvant either intraperitonealy (IP), subcutaneously (Sc) or via footpad (FP), followed by 3-21 days IP, Sc or FP immunization (up to a total of 11 immunizations) with the antigen in incomplete Freund's or Ribi adjuvant. The immune response was monitored by retroorbital bleeds. The plasma was screened by ELISA (as described below), and mice with sufficient titers of anti-IFNAR-1 human immunogolobulin were used for fusions. Mice were boosted intravenously with antigen 3 and 2 days before sacrifice and removal of the spleen. Typically, 10-35 fusions for each antigen were performed. Several dozen mice were immunized for each antigen.

Selection of HuMab Mice Producing Anti-IFNAR-1 Antibodies:

To select HuMab mice producing antibodies that bound IFNAR-1, sera from immunized mice was tested by ELISA as described by Fishwild, D. et al. (1996). Briefly, microtiter plates were coated with purified recombinant IFNAR-1 from E. coli at 1-2 µg/ml in PBS, 50 µl/wells incubated 4° C. overnight then blocked with 200 µl/well of 5% chicken serum in PBS/Tween (0.05%). Dilutions of plasma from IFNAR-1-immunized mice were added to each well and incubated for 1-2 hours at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with ABTS substrate (Sigma, A-1888, 0.22 mg/ml) and analyzed by spectrophotometer at OD 415-495. Mice that developed the highest titers of anti-IFNAR-1 antibodies were used for fusions. Fusions were performed as described below and hybridoma supernatants were tested for anti-IFNAR-1 activity by ELISA.

Generation of Hybridomas Producing Human Monoclonal Antibodies to IFNAR-1:

The mouse splenocytes, isolated from the HuMab mice, were fused with PEG to a mouse myeloma cell line based upon standard protocols. The resulting hybridomas were then screened for the production of antigen-specific antibodies. Single cell suspensions of splenic lymphocytes from immunized mice were fused to one-fourth the number of SP2/0 nonsecreting mouse myeloma cells (ATCC, CRL 1581) with 50% PEG (Sigma). Cells were plated at approximately $1 \times 10^5$/well in flat bottom microtiter plate, followed by about two week incubation in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1× HAT (Sigma, CRL P-7185). After 1-2 weeks, cells were cultured in medium in which the HAT was replaced with HT. Individual wells were then screened by ELISA (described above) for human anti-IFNAR-1 monoclonal IgG antibodies. Once extensive hybridoma growth occurred, medium was monitored usually after 10-14 days. The antibody secreting hybridomas were replated, screened again and, if still positive for human IgG, anti-IFNAR-1 monoclonal antibodies were subcloned at least twice by limiting dilution. The stable subclones were then cultured in vitro to generate small amounts of antibody in tissue culture medium for further characterization.

Hybridoma clones 3F11, 4G5, 11E2, and 9D4 were selected for further analysis.

EXAMPLE 2

Structural Characterization of Human Monoclonal Antibodies 3F11, 4G5, 11E2, and 9D4

The cDNA sequences encoding the heavy and light chain variable regions of the 3F11, 4G5, 11E2, and 9D4 monoclonal antibodies were obtained from the 3F11, 4G5, 11E2, and 9D4 hybridomas, respectively, using standard PCR techniques and were sequenced using standard DNA sequencing techniques.

The nucleotide and amino acid sequences of the heavy chain variable region of 3F11 are shown in FIG. 1A and in SEQ ID NO: 33 and 25, respectively.

The nucleotide and amino acid sequences of the light chain variable region of 3F11 are shown in FIG. 1B and in SEQ ID NO: 37 and 29, respectively.

Comparison of the 3F11 heavy chain immunoglobulin sequence to the known human germline immunoglobulin heavy chain sequences demonstrated that the 3F11 heavy chain utilizes a VH segment from human germline VH 4-34, an undetermined D segment, and a JH segment from human germline JH 6b. The alignment of the 3F11 VH sequence to the germline VH 4-34 sequence is shown in FIG. 5. Further analysis of the 3F11 VH sequence using the Kabat system of CDR region determination led to the delineation of the heavy chain CDR1, CDR2 and CD3 regions as shown in FIGS. 1A and 5, and in SEQ ID NOs: 1, 5 and 9, respectively.

Comparison of the 3F11 light chain immunoglobulin sequence to the known human germline immunoglobulin light chain sequences demonstrated that the 3F11 light chain utilizes a VL segment from human germline VK L18 and a JK segment from human germline JK 5. The alignment of the 3F11 VL sequence to the germine VK L18 sequence is shown in FIG. 8. Further analysis of the 3F11 VL sequence using the Kabat system of CDR region determination led to the delineation of the light chain CDR1, CDR2 and CD3 regions as shown in FIGS. 1B and 8, and in SEQ ID NOs:13, 17 and 21, respectively.

The nucleotide and amino acid sequences of the heavy chain variable region of 4G5 are shown in FIG. 2A and in SEQ ID NO: 34 and 26, respectively.

The nucleotide and amino acid sequences of the light chain variable region of 4G5 are shown in FIG. 2B and in SEQ ID NO: 38 and 30, respectively.

Comparison of the 4G5 heavy chain immunoglobulin sequence to the known human germline immunoglobulin heavy chain sequences demonstrated that the 4G5 heavy chain utilizes a VH segment from human germline VH 4-34, an undetermined D segment, and a JH segment from human germline JH 4b. The alignment of the 4G5 VH sequence to the germline VH 4-34 sequence is shown in FIG. 6. Further analysis of the 4G5 VH sequence using the Kabat system of CDR region determination led to the delineation of the heavy chain CDR1, CDR2 and CD3 regions as shown in FIGS. 2A and 6, and in SEQ ID NOs: 2, 6 and 10, respectively.

Comparison of the 4G5 light chain immunoglobulin sequence to the known human germline immunoglobulin light chain sequences demonstrated that the 4G5 light chain utilizes a VL segment from human germline VK L18 and a JK segment from human germline JK 2. The alignment of the 4G5 VL sequence to the germline VK L18 sequence is shown in FIG. 9. Further analysis of the 4G5 VL sequence using the Kabat system of CDR region determination led to the delineation of the light chain CDR1, CDR2 and CD3 regions as shown in FIGS. 2B and 9, and in SEQ ID NOs:14, 18 and 22, respectively.

The nucleotide and amino acid sequences of the heavy chain variable region of 11E2 are shown in FIG. 3A and in SEQ ID NO: 35 and 27, respectively.

The nucleotide and amino acid sequences of the light chain variable region of 11E2 are shown in FIG. 3B and in SEQ ID NO: 39 and 31, respectively.

Comparison of the 11E2 heavy chain immunoglobulin sequence to the known human germline immunoglobulin heavy chain sequences demonstrated that the 11E2 heavy chain was derived from, or is highly similar to, a VH segment from human germline VH 5-51, an undetermined D segment, and a JH segment from human germline JH 4b. The alignment of the 11E2 VH sequence to the germline VH 5-51 sequence is shown in FIG. 7. Further analysis of the 11E2 VH sequence using the Kabat system of CDR region determination led to the delineation of the heavy chain CDR1, CDR2 and CD3 regions as shown in FIGS. 3A and 7, and in SEQ ID NOs: 3, 7 and 11, respectively.

Comparison of the 11E2 light chain immunoglobulin sequence to the known human germline immunoglobulin light chain sequences demonstrated that the 11E2 light chain utilizes a VL segment from human germline VK A27 and a JK segment from human germline JK 5. The alignment of the 11E2 VL sequence to the germline VK A27 sequence is shown in FIG. 10. Further analysis of the 11E2 VL sequence using the Kabat system of CDR region determination led to the delineation of the light chain CDR1, CDR2 and CD3 regions as shown in FIGS. 3B and 10, and in SEQ ID NOs:15, 19 and 23, respectively.

The nucleotide and amino acid sequences of the heavy chain variable region of 9D4 are shown in FIG. 4A and in SEQ ID NO: 36 and 28, respectively.

The nucleotide and amino acid sequences of the light chain variable region of 9D4 are shown in FIG. 4B and in SEQ ID NO: 40 and 32, respectively.

Comparison of the 9D4 heavy chain immunoglobulin sequence to the known human germline immunoglobulin heavy chain sequences demonstrated that the 9D4 heavy chain was derived from, or is highly similar to, a VH segment from human germline VH 5-51, an undetermined D segment, and a JH segment from human germline JH 4b. The alignment of the 9D4 VH sequence to the germline VH 5-51 sequence is shown in FIG. 7. Further analysis of the 9D4 VH sequence using the Kabat system of CDR region determination led to the delineation of the heavy chain CDR1, CDR2 and CD3 regions as shown in FIGS. 4A and 7, and in SEQ ID NOs: 4, 8 and 12, respectively.

Comparison of the 9D4 light chain immunoglobulin sequence to the known human germline immunoglobulin light chain sequences demonstrated that the 9D4 light chain utilizes a VL segment from human germline VK A27 and a JK segment from human germline JK 5. The alignment of the 9D4 VL sequence to the germline VK A27 sequence is shown in FIG. 10. Further analysis of the 9D4 VL sequence using the Kabat system of CDR region determination led to the delin-eation of the light chain CDR1, CDR2 and CD3 regions as shown in FIGS. 3B and 10, and in SEQ ID NOs:16, 20 and 24, respectively.

EXAMPLE 3

Anti-IFNAR-1 Human Monoclonal Antibodies Inhibit the Biological Activity of Interferon α2b The cell line Daudi, derived from a human B-lymphoblast Burkitt's lymphoma, expresses high levels of IFNAR-1, and the growth of these cells is inhibited by Type I interferons. To measure the functional blocking ability of human anti-IF-NAR-1 antibodies, two different assays were performed, a cell proliferation assay and a reporter assay.

In the first assay, Daudi cells were cultured with interferon α2b in the presence or absence of antibody and proliferation was measured by uptake of $^3$[H]-thymidine. Daudi cells (ATCC CCL-213) were grown in RPMI containing 10% FCS, and 2 mM beta mercaptoethanol (media). Cells were spun and resuspended at a concentration of $1 \times 10^6$ cells/ml in media with added 1% human serum albumin (media & HS). To each well of a 96-well plate, 100 µl of 200 U/ml interferon α2b (SCHERING Corporation) containing the appropriate concentration of antibody was added. 100 µl of Daudi cells in media & HS were added to the wells and the plates were incubated for 48 hours at 37° C. The plates were pulsed with 1 µCi of $^3$[H]-thymidine and incubated for an additional 24 hours. The plates were harvested, collected onto a 96-well fiber filter plate, and counted using a TopCount scintillation counter (PACKARD). The counts per minute were plotted as a function of antibody concentration and the data was analyzed by non-linear regression, sigmoidal dose-response (variable slope) using the PRISM SOFTWARE (San Diego, Calif.).

In the second assay, U937 cells were transfected with a construct in which an Interferon Stimulated Response Element was linked to a reporter gene (ISRE-RG) and the ability of humanized anti-IFNAR-1 antibodies to block IFN-induced expression of the reporter gene was measured. The cells were grown in RPMI containing 10% FCS, and 2 mM beta mercaptoethanol (media). The cells ($1 \times 10^6$ cells/ml) were resuspended in media with added 2% human serum. 100 µl of cells was added to a 96-well plate. Antibodies were serially diluted in media containing 200 U/ml of interferon α2b (SCHERING corporation) and 100 µl was added to each well. The plates were incubated overnight at 37° C. Following this incubation, expression of the reporter gene was assessed by flow cytometry. Geometric mean fluorescent intensity was plotted as a function of antibody concentration and the data was analyzed by non-linear regression, sigmoidal dose-response (variable slope) using the PRISM SOFTWARE (San Diego, Calif).

Using the above described two assays, the potency of the 3F11 human monoclonal antibody was compared to the murine anti-IFNAR-1 antibody 64G12 (ECACC Deposit No. 92022605) and to the humanized anti-IFNAR-1 antibody D1 H3K1 (described further in U.S. Ser. No. 60/465,058). The potency of 3F11 showed a 5-10 fold greater potency than the mouse antibody and a 6-30 fold greater potency than the humanized antibody. The results are summarized in Table 1 below.

TABLE 1

Blocking ability of human anti-IFNAR-1 antibody on IFN alpha 2b

|  | Isotype | Cell Proliferation (Daudi) $EC_{50}$ (nM) | ISRE-RG Reporter (U937) $EC_{50}$ (nM) |
|---|---|---|---|
| 64G12 | m IgG1 | 3.1 | 6.0 |
| DI H3K1 | h IgG1 | 9.3 | 8.0 |
| 3F11 | h IgG1 | 0.3 | 1.2 |

EXAMPLE 4

Anti-IFNAR-1 Human Monoclonal Antibodies Inhibit the Biological Activity of IFN Omega Using the Daudi proliferation assay described above in Example 3, the ability of the human anti-IFNAR-1 antibody to inhibit IFN omega responses was tested. To each well of a 96-well plate, 100 μl of 200 U/ml interferon omega (PBL) containing the appropriate concentration of antibody was added. The human antibodies 3F11, 4G5, 11E2, and 9D4 were 4-18 times more potent (as measured by $EC_{50}$) than the mouse 64G12 antibody. The results are summarized in Table 2 below.

TABLE 2

Blocking ability of human anti-IFNAR-1 antibody on IFN omega

|  | Isotype | Cell Proliferation (Daudi) $EC_{50}$ (nM) |
|---|---|---|
| 64G12 | m IgG1 | 5.5 |
| DI H3K1 | h IgG1 | 30.7 |
| 3F11 | h IgG1 | 0.6 |
| 4G5 | h IgG1 | 1.4 |
| 11E2 | h IgG1 | 0.3 |
| 9D4 | h IgG1 | 0.3 |

EXAMPLE 5

Anti-IFNAR-1 Human Monoclonal Antibodies Inhibit the Biological Activity of Multiple Type I IFNs As described in Example 3, interferon alpha inhibits the proliferation of Daudi (Burkitts lymphoma, ATCC # CCL-213) cells in a dose dependant manner. A neutralizing antibody, which blocks interferon binding to its receptor, will restore proliferation. Using this cell proliferation assay, the specificity of the purified human anti-IFN alpha antibodies was examined by testing for blockade of natural lymphoblastoid IFNα, natural leukocyte interferon, 13 recombinant IFN alpha subtypes, IFN beta and IFN omega.

Daudi cells were grown in culture medium (RPMI 1640 supplemented with 10% FCS, 1×2-ME, L-glutamine and penicillin streptomycin) with and without the addition of IFNα in a 96 well, flat-bottomed cell culture plate. Each type I interferon tested was assayed at $EC_{50}$ and mixed with a 2-fold serial titration of anti-IFNAR-1 antibody 3F11, typically from 50 ug/ml (312 nM) through 381 μg/ml (2.4 pM). The antibody/IFN mixture was added to Daudi cells in a 96-well bottomed plate to a final density of $1 \times 10^4$ Daudi cells/100 ul/well and incubated at 37° C., 5% $CO_2$, 72 hrs. Proliferation was assayed with the addition of MTS (Promega), 20 ul/well, and O.D. at 490 nm was measured following a further 3 hour incubation. The viable cell number was proportional to the O.D. reading. Percentage blockade of interferon was calculated relative to Daudi proliferation in the absence of IFN (=100% blockade) and in the presence of IFN alone (=0% blockade). The 3F11 antibody was scored according to the degree of blockade, resulting in a profile of IFNα subtype specificity. The results demonstrated that the human anti-interferon alpha receptor 1 antibody 3F11 inhibits the action of multiple interferon alpha subtypes, including IFNα6, 2b, 2a, 1, 16, 10, 8, 5, 14, 17, 7, 4, and 21, as well as lymphoblastoid IFN, leukocyte IFN, and IFN omega. 3F11 is a lower level inhibitor of IFN beta, although inhibition of greater than 50% was observed. The % blockade and standard deviation of interferon are shown in Table 3, below.

TABLE 3

Antibody Inhibition of Multiple type I interferons 3F11 IFN Blockade (%) at 1000 × Ab

| IFN | mean | sd |
|---|---|---|
| Lymphoblastoid IFN | 94.9 | 2.9 |
| IFNα 6 | 107.1 | 6.6 |
| IFNα 2b | 101.9 | 0.4 |
| IFNα 2a | 103.1 | 3.0 |
| IFNα 1 | 111.6 | 1.9 |
| Leukocyte IFN | 109.4 | 1.4 |
| IFNα 16 | 105.7 | 1.4 |
| IFNα 10 | 96.7 | 5.5 |
| IFNα 8 | 87.5 | 2.6 |
| IFNα 5 | 105.1 | 3.9 |
| IFNα 14 | 100.3 | 1.4 |
| IFNα 17 | 99.8 | 2.4 |
| IFNα 7 | 102.8 | 3.2 |
| IFNα 4 | 100.5 | 2.5 |
| IFNα 21 | 104.4 | 2.3 |
| IFN-beta | 53.0 | 1.7 |
| IFN-omega | 107.1 | 1.3 |

EXAMPLE 6

Inhibition of IFN-induced IP-10 secretion by anti-IFNAR-1 Antibodies

The addition of IFN alpha 2b to cell culture media has been shown to induce IP-10 secretion by normal peripheral blood mononuclear cells (PBMNC). The activity of human anti-IFNAR-1 antibody 3F11 was tested for inhibition of interferon induced secretion of IP-10 by normal PBMNC cultures by an ELISA binding assay.

PBMNC's were incubated in culture medium (RPMI 1640+10% FBS+1% human serum) with leukocyte IFN, IFNα 2b, or IFN φ for 24-48 hours. Supernatants were collected and analyzed for IP-10/CXCL10 concentration using a quantitative sandwich ELISA kit (QUANTIKINE®, R&D SYSTEMS) at a 1:30 dilution according to manufacturer recommendations. The results demonstrated that the human monoclonal antibody 3F11 inhibits leukocyte IFN, recombinant IFNα 2b, and recombinant IFN φ induced secretion of IP-10 by normal PBMNC culture. These results are shown in Table 4.

TABLE 4

Antibody Inhibition of IFN-Induced IP-10 Expression on Normal PBMNC

| | Ab Treatment | | | |
|---|---|---|---|---|
| | No IFN IP-10 (pg/ml) | Leukocyte IFN IP-10 (pg/ml) | IFN alpha 2b IP-10 (pg/ml) | IFN omega IP-10 (pg/ml) |
| No antibody | 907 | 2665 | 2739 | 2904 |
| 3F11 (5 µg/ml) | 387 | 854 | 745 | 674 |
| Control Ig (5 µg/ml) | 838 | 3512 | 3117 | 3960 |

* 100 U/ml of each IFN subtype was added to the cultures

EXAMPLE 7

Anti-IFNAR-1 Human Monoclonal Antibodies Cross Competition Assay

To evaluate whether the human monoclonal antibodies bind to the same epitope as the mouse 64G12 monoclonal antibody, a cross-competition ELISA assay was used to determine whether the antibodies competed for the same binding epitope.

96-well plates were coated with soluble CHO-derived human IFNAR-1 at a concentration of 1 µg/mL in freshly prepared DPBS at 100 µl/well (Mediatech). Human monoclonal antibodies 3F11, 4G5, 11E2, and 9D4 were added at 20 µg/mL to the wells column 1 and serially diluted at a 1:2 ratio in the wells from column 1 to column 12, followed by incubation for 45 minutes. Mouse monoclonal antibody 64G12, at an $EC_{75}$ concentration of 0.3 µg/mL, was added at 50 µL per well and the plates were incubated for 30 minutes. The plates were washed 3 times with Elx 405 auto plate washer (BIO-TEK Instruments). A peroxidase affinity purified F(ab')2 goat anti-mouse IgG (Fcγspecific) antibody was diluted 1:3000 in PBS and added as the detection conjugate (Jackson ImmunoResearch Laboratories, cat. 115-036-0710). After a one hour incubation, the plates were washed 3 times with Elx 405 auto plate washer. An ABTS solution (800 µl ABTS stock, 8 µl 30% $H_2O_2$, and 100 mL citrate phosphate buffer) at 27.8 mg/mL was added to each well and incubated for 20 minutes. The plates were read at 415 nm using 490 nm as a reference wavelength. The results are shown in FIG. 11. The results demonstrate that the human anti-IFNAR-1 monoclonal antibodies, 3F11, 4G5, 11E2, and 9D4 do not compete with 64G12 for binding to IFNAR-1 and thus bind to a different epitope on IFNAR-1 than 64G12.

EXAMPLE 8

Antibody Inhibition of SLE Plasma Mediated Dendritic Cell Development

SLE plasma induces dendritic cell development from normal human monocytes. In this example, the purified monoclonal human anti-IFNAR-1 antibody, 3F11, was tested for inhibition of dendritic cell development, as assessed by the ability of the antibodies to inhibit the induction of the cell surface markers CD38, MHC Class I and CD1 3 by SLE plasma.

A 25 ml buffy coat was diluted four fold with PBS. The sample was separated into 4×50 ml conical tubes, and 15 ml of lymphocyte separation medium (ICN Biomedicals) was layered underneath. Following a 30-minute spin at 500×g, the buffy layer containing the PBMCs was removed and washed with PBS. Cells were resuspended in culture media at $4\times10^6$ cells/ml. Monocytes were isolated by incubating PBMC ($2.0\times10^7$ cells/5 ml/25 $cm^2$ flask) for 1.5 hrs at 37° C. in culture medium and then washing away non-adherent cells twice. Following the second wash the cells were cultured in media containing 1% heat inactivated human serum. Twenty five percent SLE patient plasma plus/minus neutralizing antibodies and isotype controls (30 ug/ml) were added to the culture flasks; IFN α 2b (100 & 10 iu/ml) plus 25% normal human plasma was used as a positive control for marker induction. Flasks were incubated at 37° C., 5% $CO_2$ for three to seven days. Conditioned medium was harvested from each flask and suspension cells were recovered by centrifugation at 1000 rpm on a Sorvall RTH-750 rotor. The pelleted cells were retained on ice and supernate was frozen at −80° C. for ELISA. Adherent cells were recovered from the flask with a PBS wash (2 ml), followed by 15 minute incubation in versene (3 ml), if necessary. The flask was scraped at the end of the versene incubation and the flask was finally rinsed with PBS wash (2 ml). Each of the PBS washes and the versene was combined with the cells recovered from conditioned medium harvest. The pooled cell suspension was centrifuged at 1000 rpm on a Sorvall RTH-750 rotor, the resulting pellet was resuspensed to 300 ul in staining buffer (PBS+0.1 M EDTA+2% FBS1% HS) and dispensed 100 ul/well into a V-bottom 96-well plate. The plate was pulse-centriftiged at 2800 rpm on a Sorvall RTH-750 rotor and pelleted cells were resuspended 25 µl/well in flurochrome labeled antibodies as follows: (1) mouse anti-MHC I-FITC+mouse anti-CD38-PE, and (2) isotype controls, mouse IgG-FITC+mouse IgG-PE. The plate was incubated on ice for 45 minutes, protected from light. The cells were washed three times with the addition of 200 ul staining buffer followed by pulse-celtrifugation and finally resuspended in 200 µl of 2% paraformaldehyde in PBS. Staining of dendritic cells was analyzed by flow cytometry with the BECTON DICKINSON FACSCALIBUR™. Gates were drawn on the Forward Scatter vs. Side Scatter graph to remove contaminating cells from the analysis. The anti-IFNAR-1 human monoclonal antibody 3F11 inhibits the IFN α dependent process of dendritic cell development, as demonstrated by normalized expression of cell surface markers MHC Class I, CD38, and CD123 in the presence of 3F11. The results are shown below in Table 5, wherein (A) and (B) summarize results for two representative SLE donor samples.

TABLE 5

Inhibition of Dendritic Cell Maturation (A)

Donor Plasma #40* (13.3 iU/mL**)

| Culture Conditions | MHC class I | CD123 | CD38 |
|---|---|---|---|
| | MFI | MFI | MFI |
| 0 IFN/mL | 148 | 14 | 40 |
| 10 IFN/mL | 200 | 19 | 44 |
| 100 IFN/mL | 229 | 26 | 63 |
| 0 | 206 | 22 | 47 |
| 3F11 | 115 | 13 | 32 |
| HuIgG1 (isotype control) | 194 | 22 | 62 |

TABLE 5-continued

Inhibition of Dendritic Cell Maturation (B)

| Culture Conditions | Donor Plasma #59* (75.3 iU/mL**) | | |
|---|---|---|---|
| | MHC class I | CD123 | CD38 |
| 0 IFN/mL | 229 | 11 | 58 |
| 10 IFN/mL | 271 | 12 | 86 |
| 100 IFN/mL | 294 | 13 | 112 |
| 0 | 202 | 15 | 62 |
| 3F11 | 112 | 8 | 22 |
| HuIgG1 (isotype control) | 266 | 14 | 55 |

EXAMPLE 9

Scatchard Binding Analysis of Anti-IFNAR-1 Human Antibodies to Daudi Cells or Human Peripheral Blood Mononuclear Cells Human peripheral blood mononuclear cells were prepared from fresh blood by standard protocols using Ficol separation. Daudi cells were obtained from ATCC and grown in RPMI containing 10% fetal bovine serum (FBS). The cells were washed twice with RPMI containing 10% EBS at 4 degrees and the cells were adjusted to $4\times10^7$ cells/ml in RPMI media containing 10% fetal bovine serum (binding buffer). MILLIPORE plates (MAFB NOB) were coated with 1% nonfat dry milk in water and stored a 4° C. overnight. The plates were washed with binding buffer and 25 ul of unlabeled antibody (1 000-fold excess) in binding buffer was added to control wells in a Millipore 96 well glass fiber filter plate (non-specific binding NSB). Twenty-five microliters of buffer alone was added to the maximum binding control well (total binding). Twenty-five microliters of varying concentration of $^{125}$I-anti-IFNAR-1 antibody and 25 ul of Daudi cells or human peripheral blood mononuclear cells ($4\times10^7$ cells/ml) in binding buffer were added. The plates were incubated for 2 hours at 200 RPM on a shaker at 4° C. At the completion of the incubation the MILLIPORE plates were washed twice with 0.2 ml of cold binding buffer. The filters were removed and counted in a gamma counter. Evaluation of equilibrium binding was performed using single site binding parameters with the PRISM SOFTWARE (San Diego, Calif).

Using the above Scatchard binding assay, the $K_D$ of the antibody for Daudi cells and for human peripheral blood mononuclear cells was approximately 0.2 nM and 0.5 nM, respectively.

SUMMARY OF SEQUENCE LISTING

| SEQ ID NO: | SEQUENCE |
|---|---|
| 1 | VH CDR1 a.a. 3F11 |
| 2 | VH CDR1 a.a. 4G5 |
| 3 | VH CDR1 a.a. 11E2 |
| 4 | VH CDR1 a.a. 9D4 |
| 5 | VH CDR2 a.a. 3F11 |
| 6 | VH CDR2 a.a. 4G5 |
| 7 | VH CDR2 a.a. 11E2 |
| 8 | VH CDR2 a.a. 9D4 |
| 9 | VH CDR3 a.a. 3F11 |
| 10 | VH CDR3 a.a. 4G5 |
| 11 | VH CDR3 a.a. 11E2 |
| 12 | VH CDR3 a.a. 9D4 |
| 13 | VK CDR1 a.a. 3F11 |
| 14 | VK CDR1 a.a. 4G5 |
| 15 | VK CDR1 a.a. 11E2 |
| 16 | VK CDR1 a.a. 9D4 |
| 17 | VK CDR2 a.a. 3F11 |
| 18 | VK CDR2 a.a. 4G5 |
| 19 | VK CDR2 a.a. 11E2 |
| 20 | VK CDR2 a.a. 9D4 |
| 21 | VK CDR3 a.a. 3F11 |
| 22 | VK CDR3 a.a. 4G5 |
| 23 | VK CDR3 a.a. 11E2 |
| 24 | VK CDR3 a.a. 9D4 |
| 25 | VH a.a. 3F11 |
| 26 | VH a.a. 4G5 |
| 27 | VH a.a. 11E2 |
| 28 | VH a.a. 9D4 |
| 29 | VK a.a. 3F11 |
| 30 | VK a.a. 4G5 |
| 31 | VK a.a. 11E2 |
| 32 | VK a.a. 9D4 |
| 33 | VH n.t. 3F11 |
| 34 | VH n.t. 4G5 |
| 35 | VH n.t. 11E2 |
| 36 | VH n.t. 9D4 |
| 37 | VK n.t. 3F11 |
| 38 | VK n.t. 4G5 |
| 39 | VK n.t. 11E2 |
| 40 | VK n.t. 9D4 |
| 41 | VH 4-34 germline a.a. |
| 42 | VH 5-51 germline a.a. |
| 43 | VK L18 germline a.a. |
| 44 | VK A27 germline a.a. |

We claim:

1. An isolated human monoclonal antibody, or an antigen-binding portion thereof, that specifically binds to human interferon alpha receptor 1 (IFNAR-1), wherein the antibody binds to IFNAR-1 with a Kd of $1\times10^{-10}$ M or less and exhibits the following properties:

a) inhibits the biological activity of IFN-β;

b) inhibits the activity of IFN α2b in a Daudi cell proliferation assay;

c) inhibits the activity of IFN omega in a Daudi cell proliferation assay;

d) inhibits IP-10 secretion by peripheral blood mononuclear cells induced by IFN α2b;

e) inhibits IP-10 secretion by peripheral blood mononuclear cells induced by IFN omega;

f) inhibits dendritic cell development mediated by Systemic Lupus Erythematosus plasma; and g) binds to a different epitope than murine monoclonal antibody 64G12 (ECACC Deposit No. 92022605).

2. An isolated human monoclonal antibody, or antigen binding portion thereof, wherein the antibody inhibits the biological activity of IFN-β and cross-competes for binding to human interferon alpha receptor 1 with a reference antibody, wherein the reference antibody is selected from the group consisting of:

a) an antibody comprising a heavy chain variable region comprising the amino acid sequence of SEQ ID NO: 25; and a light chain variable region comprising the amino acid sequence of SEQ ID NO: 29;

b) an antibody comprising a heavy chain variable region comprising the amino acid sequence of SEQ ID NO: 26; and a light chain variable region comprising the amino acid sequence of SEQ ID NO: 30;

c) an antibody comprising a heavy chain variable region comprising the amino acid sequence of SEQ ID NO: 27; and a light chain variable region comprising the amino acid sequence of SEQ ID NO: 31; and d) an antibody comprising a heavy chain variable region comprising the amino acid sequence of SEQ ID NO: 28; and a light chain variable region comprising the amino acid sequence of SEQ ID NO: 32.

3. The isolated human monoclonal antibody, or an antigen-binding portion thereof of claim 1 comprising a heavy chain variable region that is the product of a human $V_H$4-34 or 5-51 gene.

4. The isolated human monoclonal antibody, or an antigen-binding portion thereof of claim 1 comprising a light chain variable region that is the product of a human $V_K$ L18 or A27 gene.

5. The isolated human monoclonal antibody, or antigen-binding portion thereof of claim 3 comprising a light chain variable region that is the product of a human $V_K$ L18 or A27 gene.

6. The isolated human monoclonal antibody, or antigen-binding portion thereof, of claim 5, which comprises a heavy chain variable region that is the product of a human $V_H$ 4-34 gene and a light chain variable region that is the product of a human $V_K$ L18 gene.

7. The isolated human monoclonal antibody, or antigen-binding portion thereof, of claim 5, which comprises a heavy chain variable region that is the product of a human $V_H$5-51 gene and a light chain variable region that is the product of a human $V_K$ A27 gene.

8. The isolated human monoclonal antibody, or antigen-binding portion thereof, of claim 1, which comprises:
   (a) a human heavy chain variable region CDR1 comprising the amino acid sequence of SEQ ID NO: 1;
   (b) a human heavy chain variable region CDR2 comprising the amino acid sequence of SEQ ID NO:5;
   (c) a human heavy chain variable region CDR3 comprising the amino acid sequence of SEQ ID NO:9;
   (d) a human light chain variable region CDR1 comprising the amino acid sequence of SEQ ID NO: 13;
   (e) a human light chain variable region CDR2 comprising the amino acid sequence of SEQ ID NO: 17; and
   (f) a human light chain variable region CDR3 comprising the amino acid sequence of SEQ ID NO:21.

9. The isolated human monoclonal antibody, or antigen-binding portion thereof, of claim 1, which comprises:
   (a) a human heavy chain variable region CDR1 comprising the amino acid sequence of SEQ ID NO:2;
   (b) a human heavy chain variable region CDR2 comprising the amino acid sequence of SEQ ID NO:6;
   (c) a human heavy chain variable region CDR3 comprising the amino acid sequence of SEQ ID NO: 10;
   (d) a human light chain variable region CDR1 comprising the amino acid sequence of SEQ ID NO: 14;
   (e) a human light chain variable region CDR2 comprising the amino acid sequence of SEQ ID NO: 18; and
   (f) a human light chain variable region CDR3 comprising the amino acid sequence of SEQ ID NO:22.

10. The isolated human monoclonal antibody, or antigen-binding portion thereof, of claim 1, which comprises:
    (a) a human heavy chain variable region CDR1 comprising the amino acid sequence of SEQ ID NO:3;
    (b) a human heavy chain variable region CDR2 comprising the amino acid sequence of SEQ ID NO:7;
    (c) a human heavy chain variable region CDR3 comprising the amino acid sequence of SEQ ID NO: 11;
    (d) a human light chain variable region CDR1 comprising the amino acid sequence of SEQ ID NO: 15;
    (e) a human light chain variable region CDR2 comprising the amino acid sequence of SEQ ID NO: 19; and
    (f) a human light chain variable region CDR3 comprising the amino acid sequence of SEQ ID NO:23.

11. The isolated human monoclonal antibody, or antigen-binding portion thereof, of claim 1, which comprises:
    (a) a human heavy chain variable region CDR1 comprising the amino acid sequence of SEQ ID NO:4;
    (b) a human heavy chain variable region CDR2 comprising the amino acid sequence of SEQ ID NO:8;
    (c) a human heavy chain variable region CDR3 comprising the amino acid sequence of SEQ ID NO: 12;
    (d) a human light chain variable region CDR1 comprising the amino acid sequence of SEQ ID NO: 16;
    (e) a human light chain variable region CDR2 comprising the amino acid sequence of SEQ ID NO:20; and
    (f) a human light chain variable region CDR3 comprising the amino acid sequence of SEQ ID NO:24.

12. The isolated human monoclonal antibody, or antigen-binding portion thereof, of claim 1, which comprises:
    (a) a human heavy chain variable region comprising the amino acid sequence of SEQ ID NO:25; and
    (b) a human light chain variable region comprising the amino acid sequence of SEQ ID NO:29.

13. The isolated human monoclonal antibody, or antigen-binding portion thereof, of claim 1, which comprises:
    (a) a human heavy chain variable region comprising the amino acid sequence of SEQ ID NO:26; and
    (b) a human light chain variable region comprising the amino acid sequence of SEQ ID NO:30.

14. The isolated human monoclonal antibody, or antigen-binding portion thereof, of claim 1, which comprises:
    (a) a human heavy chain variable region comprising the amino acid sequence of SEQ ID NO:27; and
    (b) a human light chain variable region comprising the amino acid sequence of SEQ ID NO:31.

15. The isolated human monoclonal antibody, or antigen-binding portion thereof, of claim 1, which comprises:
    (a) a human heavy chain variable region comprising the amino acid sequence of SEQ ID NO:28; and
    (b) a human light chain variable region comprising the amino acid sequence of SEQ ID NO:32.

16. A composition comprising the isolated human monoclonal antibody, or antigen-binding portion thereof, of claim 1, and a pharmaceutically acceptable carrier.

17. An isolated human monoclonal antibody, or an antigen-binding portion thereof, that specifically binds to human interferon alpha receptor 1 (IFNAR-I), wherein said antibody comprises:
    (a) a human heavy chain variable CDR3 region comprising the amino acid sequence of SEQ ID NO: 12; and
    (b) a human light chain variable CDR3 region comprising the amino acid sequence of SEQ ID NO:24.

18. An isolated human monoclonal antibody, or an antigen binding portion thereof, which inhibits the biological activity of IFN-β and binds an epitope on the human IFNAR-1 polypeptide recognized by an antibody selected from the group consisting of:
    (a) an antibody comprising a heavy chain variable region comprising the amino acid sequence of SEQ ID NO:28 and a light chain variable region comprising the amino acid sequence of SEQ ID NO:32;

(b) an antibody comprising a heavy chain variable region comprising the amino acid sequence of SEQ ID NO:25 and a light chain variable region comprising the amino acid sequence of SEQ ID NO:29;

(c) an antibody comprising a heavy chain variable region comprising the amino acid sequence of SEQ ID NO:26 and a light chain variable region comprising the amino acid sequence of SEQ ID NO:30; and (d) an antibody comprising a heavy chain variable region comprising the amino acid sequence of SEQ ID NO:27 and a light chain variable region comprising the amino acid sequence of SEQ ID NO:31.

19. An isolated human monoclonal antibody, or an antigen-binding portion thereof, that specifically binds to human interferon alpha receptor 1 (IFNAR-I), wherein the antibody (a) binds to IFNAR-1 with a Kd of $1 \times 10^{-10}$ M or less;

(b) inhibits the biological activity of IFN-β; and (c) does not bind the same epitope as mouse monoclonal antibody 64612 (ECACC Deposit No. 92022605).

20. A method for preparing an isolated anti-IFNAR-1 antibody comprising:

(a) providing: (i) a heavy chain variable region antibody sequence comprising a CDR1 sequence that is selected from the group consisting of SEQ ID NOS: 1, 2, 3 and 4, a CDR2 sequence that is selected from the group consisting of SEQ ID NOS: 5, 6,7, and 8; and a CDR3 sequence that is selected from the group consisting of SEQ ID NOS: 9, 10, 11, and 12; or (ii) a light chain variable region antibody sequence comprising a CDR1 sequence that is selected from the group consisting of SEQ ID NOS: 13, 14, 15, and 16, a CDR2 sequence that is selected from the group consisting of SEQ ID NOS: 17, 18, 19, and 20 and a CDR3 sequence that is selected from the group consisting of SEQ ID NOS: 21, 22, 23, and 24; and (b) expressing the antibody sequence as a protein.

\* \* \* \* \*

UNITED STATES PATENT AND TRADEMARK OFFICE
CERTIFICATE OF CORRECTION

| | |
|---|---|
| PATENT NO. | : 7,662,381 B2 |
| APPLICATION NO. | : 11/157494 |
| DATED | : February 16, 2010 |
| INVENTOR(S) | : Josephine M. Cardarelli, Alison Witte and Mohan Srinivasan |

It is certified that error appears in the above-identified patent and that said Letters Patent is hereby corrected as shown below:

IN THE SPECIFICATION:

Please insert, in column 1, Line 3; under the Title, the following:

--CROSS REFERENCE TO RELATED APPLICATIONS--

IN THE CLAIMS:

At Column 74, Line 57-58:

"antigen binding" should read --antigen-binding--

At Column 76, Line 55:

"(IFNAR-I)" should read --(IFNAR-1)--

At Column 76, Line 61-62:

"antigen binding" should read --antigen-binding--

At Column 77, Line 18:

"(IFNAR-I)" should read --(IFNAR-1)--

At Column 78, Line 9:

"6,7," should read --6, 7--

Signed and Sealed this
Fourth Day of January, 2011

David J. Kappos
*Director of the United States Patent and Trademark Office*

SEQUENCE LISTING

<160> NUMBER OF SEQ ID NOS: 44

<210> SEQ ID NO 1
<211> LENGTH: 5
<212> TYPE: PRT
<213> ORGANISM: Homo sapiens

<400> SEQUENCE: 1

Gly Tyr Phe Trp Ser
1               5

<210> SEQ ID NO 2
<211> LENGTH: 5
<212> TYPE: PRT
<213> ORGANISM: Homo sapiens

<400> SEQUENCE: 2

Asn Tyr Tyr Trp Ser
1               5

<210> SEQ ID NO 3
<211> LENGTH: 5
<212> TYPE: PRT
<213> ORGANISM: Homo sapiens

<400> SEQUENCE: 3

Asn Tyr Trp Ile Ala
1               5

<210> SEQ ID NO 4
<211> LENGTH: 5
<212> TYPE: PRT
<213> ORGANISM: Homo sapiens

<400> SEQUENCE: 4

Asn Tyr Trp Ile Ala
1               5

<210> SEQ ID NO 5
<211> LENGTH: 16
<212> TYPE: PRT
<213> ORGANISM: Homo sapiens

<400> SEQUENCE: 5

Glu Ile Asp His Ser Gly Lys Thr Asn Tyr Asn Pro Ser Leu Lys Ser
1               5                   10                  15

<210> SEQ ID NO 6
<211> LENGTH: 16
<212> TYPE: PRT
<213> ORGANISM: Homo sapiens

<400> SEQUENCE: 6

Glu Ile Ile Leu Ser Gly Ser Thr Asn Tyr Asn Pro Ser Leu Lys Ser
1               5                   10                  15

<210> SEQ ID NO 7
<211> LENGTH: 17
<212> TYPE: PRT
<213> ORGANISM: Homo sapiens

<400> SEQUENCE: 7

Ile Ile Tyr Pro Gly Asp Ser Asp Ile Arg Tyr Ser Pro Ser Phe Gln
1               5                   10                  15

Gly

<210> SEQ ID NO 8
<211> LENGTH: 17
<212> TYPE: PRT
<213> ORGANISM: Homo sapiens

<400> SEQUENCE: 8

Ile Ile Tyr Pro Gly Asp Ser Asp Ile Arg Tyr Ser Pro Ser Phe Gln
1               5                   10                  15

Gly

<210> SEQ ID NO 9
<211> LENGTH: 10
<212> TYPE: PRT
<213> ORGANISM: Homo sapiens

<400> SEQUENCE: 9

Glu Ser Lys Tyr Tyr Phe Gly Leu Asp Val
1               5                   10

<210> SEQ ID NO 10
<211> LENGTH: 10
<212> TYPE: PRT
<213> ORGANISM: Homo sapiens

<400> SEQUENCE: 10

Glu Ser Lys Trp Gly Tyr Tyr Phe Asp Ser
1               5                   10

<210> SEQ ID NO 11
<211> LENGTH: 8
<212> TYPE: PRT
<213> ORGANISM: Homo sapiens

<400> SEQUENCE: 11

His Asp Ile Glu Gly Phe Asp Tyr
1               5

<210> SEQ ID NO 12
<211> LENGTH: 8
<212> TYPE: PRT
<213> ORGANISM: Homo sapiens

<400> SEQUENCE: 12

His Asp Ile Glu Gly Phe Asp Tyr
1               5

<210> SEQ ID NO 13
<211> LENGTH: 11
<212> TYPE: PRT
<213> ORGANISM: Homo sapiens

<400> SEQUENCE: 13

Arg Ala Ser Gln Gly Ile Tyr Ser Val Leu Ala
1               5                   10

<210> SEQ ID NO 14
<211> LENGTH: 11
<212> TYPE: PRT
<213> ORGANISM: Homo sapiens

<400> SEQUENCE: 14

Arg Ala Thr Gln Asp Ile Ser Ile Ala Leu Val
1               5                   10

<210> SEQ ID NO 15
<211> LENGTH: 12
<212> TYPE: PRT
<213> ORGANISM: Homo sapiens

<400> SEQUENCE: 15

Arg Ala Ser Gln Ser Val Ser Ser Ser Phe Phe Ala
1               5                   10

<210> SEQ ID NO 16
<211> LENGTH: 12
<212> TYPE: PRT
<213> ORGANISM: Homo sapiens

<400> SEQUENCE: 16

Arg Ala Ser Gln Ser Val Ser Ser Ser Phe Phe Ala
1               5                   10

<210> SEQ ID NO 17
<211> LENGTH: 7
<212> TYPE: PRT
<213> ORGANISM: Homo sapiens

<400> SEQUENCE: 17

Asp Ala Ser Arg Leu Glu Ser
1               5

<210> SEQ ID NO 18
<211> LENGTH: 7
<212> TYPE: PRT
<213> ORGANISM: Homo sapiens

<400> SEQUENCE: 18

Asp Ala Ser Gly Leu Gly Ser
1               5

<210> SEQ ID NO 19
<211> LENGTH: 7
<212> TYPE: PRT
<213> ORGANISM: Homo sapiens

<400> SEQUENCE: 19

Gly Ala Ser Ser Arg Ala Thr
1               5

<210> SEQ ID NO 20
<211> LENGTH: 7
<212> TYPE: PRT
<213> ORGANISM: Homo sapiens

<400> SEQUENCE: 20

Gly Ala Ser Ser Arg Ala Thr
1               5

<210> SEQ ID NO 21
<211> LENGTH: 8
<212> TYPE: PRT
<213> ORGANISM: Homo sapiens

<400> SEQUENCE: 21

Gln Gln Phe Asn Ser Tyr Ile Thr
1               5

<210> SEQ ID NO 22
<211> LENGTH: 9
<212> TYPE: PRT
<213> ORGANISM: Homo sapiens

<400> SEQUENCE: 22

Gln Gln Phe Asn Ser Tyr Pro Tyr Thr
1               5

```
<210> SEQ ID NO 23
<211> LENGTH: 9
<212> TYPE: PRT
<213> ORGANISM: Homo sapiens

<400> SEQUENCE: 23

Gln Gln Tyr Asp Ser Ser Ala Ile Thr
1               5

<210> SEQ ID NO 24
<211> LENGTH: 9
<212> TYPE: PRT
<213> ORGANISM: Homo sapiens

<400> SEQUENCE: 24

Gln Gln Tyr Asp Ser Ser Ala Ile Thr
1               5

<210> SEQ ID NO 25
<211> LENGTH: 118
<212> TYPE: PRT
<213> ORGANISM: Homo sapiens

<400> SEQUENCE: 25

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Phe Trp Ser Trp Ile Arg Gln Pro Pro Gly Lys Gly Leu Glu Trp Ile
        35                  40                  45

Gly Glu Ile Asp His Ser Gly Lys Thr Asn Tyr Asn Pro Ser Leu Lys
    50                  55                  60

Ser Arg Val Thr Ile Ser Val Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Ser Lys Tyr Tyr Phe Gly Leu Asp Val Trp Gly Gln Gly Thr
            100                 105                 110

Thr Val Thr Val Thr Ser
        115

<210> SEQ ID NO 26
<211> LENGTH: 118
<212> TYPE: PRT
<213> ORGANISM: Homo sapiens

<400> SEQUENCE: 26

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asn Tyr
            20                  25                  30

Tyr Trp Ser Trp Ile Arg Gln Pro Pro Gly Lys Gly Leu Glu Trp Ile
        35                  40                  45

Gly Glu Ile Ile Leu Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Thr Ser Val Thr Ala Ala Asp Thr Ala Val Tyr Tyr Cys Ala
                85                  90                  95
```

Arg Glu Ser Lys Trp Gly Tyr Tyr Phe Asp Ser Trp Gly Gln Gly Thr
                100                 105                 110

Leu Val Thr Val Ser Ser
            115

<210> SEQ ID NO 27
<211> LENGTH: 117
<212> TYPE: PRT
<213> ORGANISM: Homo sapiens

<400> SEQUENCE: 27

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
            20                  25                  30

Trp Ile Ala Trp Val Arg Gln Met Pro Gly Lys Gly Leu Glu Ser Met
        35                  40                  45

Gly Ile Ile Tyr Pro Gly Asp Ser Asp Ile Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Ile Glu Gly Phe Asp Tyr Trp Gly Arg Gly Thr Leu
            100                 105                 110

Val Thr Val Ser Ser
            115

<210> SEQ ID NO 28
<211> LENGTH: 117
<212> TYPE: PRT
<213> ORGANISM: Homo sapiens

<400> SEQUENCE: 28

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
            20                  25                  30

Trp Ile Ala Trp Val Arg Gln Met Pro Gly Lys Gly Leu Glu Ser Met
        35                  40                  45

Gly Ile Ile Tyr Pro Gly Asp Ser Asp Ile Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Ile Glu Gly Phe Asp Tyr Trp Gly Arg Gly Thr Leu
            100                 105                 110

Val Thr Val Ser Ser
            115

<210> SEQ ID NO 29
<211> LENGTH: 106
<212> TYPE: PRT
<213> ORGANISM: Homo sapiens

<400> SEQUENCE: 29

Ala Ile Gln Leu Thr Gln Ser Pro Ser Ser Leu Ser Ala Ser Val Gly

```
                1               5                  10                 15

Asp Arg Val Thr Ile Thr Cys Arg Ala Ser Gln Gly Ile Tyr Ser Val
                20                 25                 30

Leu Ala Trp Tyr Gln Gln Lys Pro Gly Lys Thr Pro Lys Leu Leu Ile
                35                 40                 45

Tyr Asp Ala Ser Arg Leu Glu Ser Gly Val Pro Ser Arg Phe Ser Gly
                50                 55                 60

Ser Gly Ser Gly Thr Asp Phe Thr Leu Thr Ile Ser Ser Leu Gln Pro
65                      70                 75                 80

Glu Asp Phe Ala Thr Tyr Tyr Cys Gln Gln Phe Asn Ser Tyr Ile Thr
                85                 90                 95

Phe Gly Gln Gly Thr Arg Leu Glu Ile Lys
                100                105

<210> SEQ ID NO 30
<211> LENGTH: 107
<212> TYPE: PRT
<213> ORGANISM: Homo sapiens

<400> SEQUENCE: 30

Ala Ile Gln Leu Thr Gln Ser Pro Ser Ser Leu Ser Ala Ser Val Gly
1               5                  10                 15

Asp Arg Val Thr Ile Thr Cys Arg Ala Thr Gln Asp Ile Ser Ile Ala
                20                 25                 30

Leu Val Trp Tyr Gln Gln Lys Pro Gly Lys Ala Pro Glu Leu Leu Ile
                35                 40                 45

Tyr Asp Ala Ser Gly Leu Gly Ser Gly Val Pro Ser Arg Phe Ser Gly
                50                 55                 60

Ser Gly Ser Gly Thr Asp Phe Thr Leu Thr Ile Ser Ser Leu Gln Pro
65                      70                 75                 80

Glu Asp Phe Ala Thr Tyr Tyr Cys Gln Gln Phe Asn Ser Tyr Pro Tyr
                85                 90                 95

Thr Phe Gly Gln Gly Thr Lys Leu Glu Ile Lys
                100                105

<210> SEQ ID NO 31
<211> LENGTH: 108
<212> TYPE: PRT
<213> ORGANISM: Homo sapiens

<400> SEQUENCE: 31

Glu Ile Val Leu Thr Gln Ser Pro Gly Thr Leu Ser Leu Ser Pro Gly
1               5                  10                 15

Glu Arg Ala Thr Leu Ser Cys Arg Ala Ser Gln Ser Val Ser Ser Ser
                20                 25                 30

Phe Phe Ala Trp Tyr Gln Gln Lys Pro Gly Gln Ala Pro Arg Leu Leu
                35                 40                 45

Ile Tyr Gly Ala Ser Ser Arg Ala Thr Gly Ile Pro Asp Arg Leu Ser
                50                 55                 60

Gly Ser Gly Ser Gly Thr Asp Phe Thr Leu Thr Ile Thr Arg Leu Glu
65                      70                 75                 80

Pro Glu Asp Phe Ala Val Tyr Tyr Cys Gln Gln Tyr Asp Ser Ser Ala
                85                 90                 95

Ile Thr Phe Gly Gln Gly Thr Arg Leu Glu Ile Lys
                100                105
```

<210> SEQ ID NO 32
<211> LENGTH: 108
<212> TYPE: PRT
<213> ORGANISM: Homo sapiens

<400> SEQUENCE: 32

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Leu Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Asp Ser Ser Ala
                85                  90                  95

Ile Thr Phe Gly Gln Gly Thr Arg Leu Glu Ile Lys
            100                 105

<210> SEQ ID NO 33
<211> LENGTH: 354
<212> TYPE: DNA
<213> ORGANISM: Homo sapiens

<400> SEQUENCE: 33
caggtgcagc tacagcagtg gggcgcagga ctgttgaagc cttctgagac cctgtccctc        60
acctgcgctg tctatggtgg gtccttcagt ggttatttct ggagctggat ccgccagccc       120
ccagggaagg gctggagtg gattggggaa atcgatcaca gtggaaagac caactacaat        180
ccgtccctca agagtcgagt taccatatca gtagacacgt ccaagaacca ggtctccctg       240
aagctgagct ctgtgaccgc cgcggacacg gctgtgtatt actgtgcgag agaaagcaag       300
tactacttcg gtttggacgt ctggggccaa gggaccacgg tcaccgtcac ctca             354

<210> SEQ ID NO 34
<211> LENGTH: 354
<212> TYPE: DNA
<213> ORGANISM: Homo sapiens

<400> SEQUENCE: 34
caggtgcagc tacagcagtg gggcgcagga ctgttgaagc cttcggagac cctgtccctc        60
acctgcgctg tctatggtgg gtccttcagt aattactact ggagctggat ccgccagccc       120
ccagggaagg gctggagtg gattggggaa atcattctta gtggaagcac caactacaac        180
ccgtccctca agagtcgagt caccatatca gtagacacgt ccaagaacca gttctccctg       240
aacctgacct ctgtgaccgc cgcggacacg gctgtgtatt actgtgcgag agtctctaaa       300
tggggttact actttgactc ctggggccag ggaaccctgg tcaccgtctc ctca             354

<210> SEQ ID NO 35
<211> LENGTH: 351
<212> TYPE: DNA
<213> ORGANISM: Homo sapiens

<400> SEQUENCE: 35
gaggtgcagc tggtgcagtc tggagcagag gtgaaaaagc ccggggagtc tctgaagatc        60
tcctgtaagg gttctggata catctttacc aattactgga tcgcctgggt gcgccagatg       120

```
cccggtaaag gcctggagtc gatggggatc atctatcctg gtgactctga tatcagatac      180
agcccgtcct tccaaggcca ggtcaccatc tcagccgaca agtccatcac caccgcctac      240
ctgcagtgga gcagtctgaa ggcctcagac accgccatgt attactgtgc gagacatgac      300
atagaggggt ttgactactg gggccgggga accctggtca ccgtctcctc a               351

<210> SEQ ID NO 36
<211> LENGTH: 318
<212> TYPE: DNA
<213> ORGANISM: Homo sapiens

<400> SEQUENCE: 36
gccatccagt tgacccagtc tccatcctcc ctgtctgcat ctgtaggaga cagagtcacc      60
atcacttgcc gggcaagtca gggcatttac agtgttttag cctggtatca gcagaaacca      120
gggaaaactc ctaagctcct gatctatgat gcctcccgtt tggaaagtgg ggtcccatca      180
aggttcagcg gcagtggatc tgggacagat ttcactctca ccatcagcag cctgcagcct      240
gaagattttg caacttatta ctgtcaacag tttaatagtt acatcacctt cggccaaggg      300
acacgactgg agattaaa                                                    318

<210> SEQ ID NO 37
<211> LENGTH: 351
<212> TYPE: DNA
<213> ORGANISM: Homo sapiens

<400> SEQUENCE: 37
gaggtgcagc tggtgcagtc tggagcagag gtgaaaaagc ccggggagtc tctgaagatc      60
tcctgtaagg gttctggata catctttacc aactactgga tcgcctgggt gcgccagatg      120
cccggtaaag gcctggagtc gatggggatc atctatcctg gtgactctga tatcagatac      180
agcccgtcct tccaaggcca ggtcaccatc tcagccgaca agtccatcac caccgcctac      240
ctgcagtgga gcagtctgaa ggcctcagac accgccatgt attactgtgc gagacatgac      300
atagaggggt ttgactactg gggccgggga accctggtca ccgtctcctc a               351

<210> SEQ ID NO 38
<211> LENGTH: 320
<212> TYPE: DNA
<213> ORGANISM: Homo sapiens

<400> SEQUENCE: 38
gccatccagt tgacccagtc tccatcctcc ctgtctgcat ctgtaggaga cagagtcacc      60
atcacttgcc gggcaactca ggacattagc attgctttag tctggtatca gcagaaacca      120
gggaaagctc ctgagctcct gatctatgat gcctccggtt tgggaagtgg ggtcccatca      180
aggttcagcg gcagtggatc tgggacagat ttcactctca ccatcagcag cctgcagcct      240
gaagattttg caacttatta ctgtcaacag ttaatagtta cccgtacact tttggccagg      300
ggaccaagct ggagatcaaa                                                  320

<210> SEQ ID NO 39
<211> LENGTH: 324
<212> TYPE: DNA
<213> ORGANISM: Homo sapiens

<400> SEQUENCE: 39
gaaattgtgt tgacgcagtc tccaggcacc ctgtctttgt ctccagggga aagagccacc      60
```

-continued

```
ctctcctgca gggccagtca gagtgttagc agcagcttct tcgcctggta ccagcagaaa    120
cctggccagg ctcccaggct cctcatctat ggtgcatcca gcagggccac tggcatccca    180
gacaggttaa gtggcagtgg gtctgggaca gacttcactc tcaccatcac cagactggag    240
cctgaagatt ttgcagtgta ttactgtcag cagtatgata gctcagcgat caccttcggc    300
caagggacac gactggagat taaa                                            324
```

<210> SEQ ID NO 40
<211> LENGTH: 324
<212> TYPE: DNA
<213> ORGANISM: Homo sapiens

<400> SEQUENCE: 40

```
gaaattgtgt tgacgcagtc tccaggcacc ctgtctttgt ctccagggga aagagccacc     60
ctctcctgca gggccagtca gagtgttagc agcagcttct tcgcctggta ccagcagaaa    120
cctggccagg ctcccaggct cctcatctat ggtgcatcca gcagggccac tggcatccca    180
gacaggttaa gtggcagtgg gtctgggaca gacttcactc tcaccatcac cagactggag    240
cctgaagatt ttgcagtgta ttactgtcag cagtatgata gctcagcgat caccttcggc    300
caagggacac gactggagat taaa                                            324
```

<210> SEQ ID NO 41
<211> LENGTH: 97
<212> TYPE: PRT
<213> ORGANISM: Homo sapiens

<400> SEQUENCE: 41

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg
```

<210> SEQ ID NO 42
<211> LENGTH: 98
<212> TYPE: PRT
<213> ORGANISM: Homo sapiens

<400> SEQUENCE: 42

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
```

-continued

```
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 43
<211> LENGTH: 95
<212> TYPE: PRT
<213> ORGANISM: Homo sapiens

<400> SEQUENCE: 43

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                85                  90                  95

<210> SEQ ID NO 44
<211> LENGTH: 95
<212> TYPE: PRT
<213> ORGANISM: Homo sapiens

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro
                85                  90                  95
```